United States Patent
Roe et al.

(10) Patent No.: US 7,365,065 B2
(45) Date of Patent: Apr. 29, 2008

(54) NON-PEPTIDE GNRH ANTAGONISTS

(75) Inventors: Michael Bryan Roe, Southampton (GB); Andrzej Roman Batt, Southampton (GB); David Michael Evans, Suthampton (GB); Gary Robert William Pitt, Hampshire (GB); David Philip Rooker, Hampshire (GB)

(73) Assignee: Ferring B.V., Hoofddrop (NL)

( * ) Notice: Subject to any disclaimer, the term of this patent is extended or adjusted under 35 U.S.C. 154(b) by 269 days.

(21) Appl. No.: 10/507,595

(22) PCT Filed: Mar. 12, 2003

(86) PCT No.: PCT/GB03/01042

§ 371 (c)(1),
(2), (4) Date: Apr. 28, 2005

(87) PCT Pub. No.: WO03/078398

PCT Pub. Date: Sep. 25, 2003

(65) Prior Publication Data

US 2005/0222139 A1 Oct. 6, 2005

(30) Foreign Application Priority Data

Mar. 15, 2002 (GB) .................................. 0206219.8

(51) Int. Cl.
*C07D 215/08* (2006.01)
*C07D 413/06* (2006.01)
*C07D 413/14* (2006.01)
*A61K 31/538* (2006.01)

(52) U.S. Cl. .................................... 514/230.5; 544/105

(58) Field of Classification Search ............. 514/230.5; 544/105
See application file for complete search history.

(56) References Cited

FOREIGN PATENT DOCUMENTS

WO    WO 00 53178 A    9/2000

OTHER PUBLICATIONS

International Search Report.
International Search Report (Jun. 16, 2003).

*Primary Examiner*—Kahsay T. Habte
(74) *Attorney, Agent, or Firm*—Foley & Lardner LLP

(57) ABSTRACT

Compounds according to general formula 1, wherein $A^1$-$A^3$ are selected from $A^5$ and $A^6$ where $A^5$ is either =$CR^{13}$— or =N— and $A^6$ is —$NR^{14}$—, —O— or —S—; $A^4$ is either a covalent bond or $A^5$, provided that when $A^4$ is a covalent bond one of $A^1$-$A^3$ must be $A^6$ and the other two must be $A^5$ and when $A^4$ is $A^5$ then all of $A^1$-$A^3$ must be $A^5$; $R^1$ is selected from H, NHY' and $COY^2$, in which case $R^2$ is H, or $R^1$ and R2 may both be methyl or together represent =O; $R^3$, $R^4$ and $R^5$ are each independently selected from H and lower alkyl groups; $R^6$, $R^7$, $R^8$, $R^9$, $R^{10}$, $R^{11}$ and $R^{12}$ are each independently selected from H, lower alkyl groups, $NH_2$, halogens (F, Cl and Br) O-alkyl, $CH_2NM_2$ and $CF^3$; $R^{13}$ is selected from H, F, Cl Br, $NO_2$, $NH_2$, OH, Me, Et, OMe, $NMe_2$ and $CF^3$; $R^{14}$ is selected from H, methyl and ethyl; W is selected from =CH— and =N—; X is selected from $CH_2$, O, S, $SO_2$, NH and N lower alkyl; $Y^1$ is selected from CO-lower alkyl, $CO(CH_2)_bY^3$, $CO(CH_2)_bCOY^3$ and $CO(CH)NHCOY^3$, where b is 1-3; Y2 is selected from $OR^{15}$, $NR^{16}R^{17}$ and $NH(CH_2)_cCOY^3$, where c is 1-3; $Y^3$ is selected from $OR^{15}$ and $NR^{16}R^{17}$; $R^{15}$ is selected from H, lower alkyl and $(CH_2)_aR^{16}$, where a is 0-4; $R^{16}$ and $R^{17}$ are each independently selected from H, lower alkyl and $(CH_2)_a R^{16}$ or together are —$(CH_2)_2$-Z-$(CH_2)_2$—; $R^{18}$ is OH a phenyl group or an aromatic heterocycle selected from pyridyl, pyrimidinyl, pyrazinyl, furyl, thienyl, pyrrolyl, imidazolyl, pyrazolyl, oxazolyl, isoxazolyl, thiazolyl, isothiazolyl, triazolyl, oxadiazolyl and thiadiazolyl, each of which may optionally have a lower alkyl group substituent; and Z is selected from O, $CH_2$, S, $SO_2$, NH and N-lower alkyl, are new. They are useful in the treatment of breast and prostate cancer, endometriosis and benign prostate hyperplasia, in the regulation of fertility, and in in vitro fertilisation.

25 Claims, No Drawings

NON-PEPTIDE GNRH ANTAGONISTS

The present invention relates to a series of compounds that act as antagonists at the GnRH receptor. The compounds are useful in the treatment of endometriosis and hormone-dependent cancers, and in the control of ovulation during in vitro fertilisation protocols.

BACKGROUND

Gonadotropin Releasing Hormone (GnRH, also known as Luteinizing Hormone Releasing Hormone, LHRH) is a decapeptide hormone produced in the hypothalamus. Upon release it is transported to the pituitary, where it causes the secretion of Follicle Stimulating Hormone (FSH) and Luteinizing Hormone (LH). These two hormones then act at the ovaries (in females) or the testes (in males). They control folliculogenesis and ovulation in females and the release of steroid hormones in both males and females.

It is widely recognised that over-secretion of steroid hormones can be detrimental to the health. For example, certain neoplasms (such as breast and prostate cancer) and endometriosis are promoted by high steroid levels. Agents that modulate the hypothalamic-pituitary-gonadal axis are therefore of therapeutic interest. The first compounds used clinically were GnRH super-agonists. These are analogues of GnRH that retain all the biological actions of the native hormone, but which are administered in such a way as to cause chronic activation of the GnRH receptors. Within a period of a few days this chronic activation causes down-regulation of the receptor signaling, and FSH and LH levels fall. The disadvantage with these agents is that, in the first few days, they cause an over-production of FSH and LH which can result in a "flare" reaction. Because of this, attention then moved to the development of GnRH antagonists. Modification of the peptide sequence has led to the discovery of a number of peptide antagonists that are now in clinical trials. However, because these compounds are still peptides, they must be given parenterally (usually by subcutaneous or intramuscular injection). They are also relatively expensive to make and purify. Accordingly, there exists a need for therapeutically effective non-peptide GnRH antagonists, and particularly for compounds that can be administered orally and that are inexpensive.

BRIEF DESCRIPTION OF THE INVENTION

We disclose herein a series of aryl sulphonamides that are potent and selective antagonists at the GnRH receptor. Accordingly, in a first aspect, the present invention comprises compounds which are derivatives according to general formula 1, and pharmaceutically acceptable salts thereof.

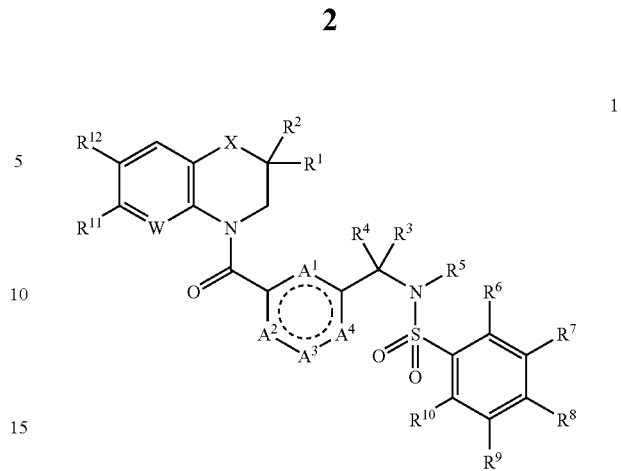

In this general structure $A^1$-$A^3$ each may be selected from $A^6$ and $A^6$, where $A^5$ may be either =$CR^{13}$— or N— and A_may be —$NR^{14}$—, —O— or —S—. $A^4$ may be either a covalent bond or $A^5$. When $A^4$ is a covalent bond, such that the ring including $A^1$-$A^4$ is a five-membered ring, one of $A^1$-$A^3$ must be $A^6$ and the other two must be $A^5$. When $A^4$ is $A^5$, such that the ring is a six-membered ring, then all of $A^1$-$A^3$ must be $A^5$. The group $R^1$ may be selected from H (a hydrogen atom), $NHY^1$ and $COY^2$. In any of these cases the group $R^2$ is H. Alternatively, $R^1$ and $R^2$ may both be methyl groups or together may represent =O so as to form a carbonyl group. The groups $R^3$, $R^4$ and $R^5$ are each independently selected from H, lower alkyl and lower alkenyl groups. The groups $R^6$, $R^7$, $R^8$, $R^9$, $R^{10}$, $R^{11}$ and $R^{12}$ are each independently selected from H, lower alkyl groups, lower alkenyl groups, $NH_2$, halogens (F, Cl and Br) O-alkyl, O-lower alkyl, O-lower alkenyl, $CH_2NMe_2$ and $CF_3$. The group $R^{13}$ is selected from H, F, Cl, Br, $NO_2$, $NH_2$, OH, Me, Et, OMe, $NM_2$ and $CF_3$. The group $R^{14}$ is selected from H, methyl and ethyl. W is selected from =CH— and =N—. X is selected from $CH_2$, O, S, $SO_2$, NH, N-lower alkyl and N-lower alkenyl groups. The group $Y^1$ is selected from CO-lower alkyl, CO-lower alkenyl, $CO(CH_2)_bY^3$, $CO(CH_2)_b$ $COY^3$ and $CO(CH_2)_b NHCOY^3$, where b is 1-3. The group $Y^2$ is selected from $OR^{15}$, $NR^{16}R^{17}$ and $NH(CH_2)_c$ $COY^3$, where c is 1-3. The group $Y^3$ is selected from alkyl, lower alkenyl, $OR^{15}$ and $NR^{16}R^{17}$. The group $R^{15}$ is selected from H, lower alkyl, lower alkenyl, and $(CH^2)_a R^{18}$ where a is 0-4. The groups $R^{16}$ and $R^{17}$ are each independently selected from H, lower alkyl and $(CH_2)_a R^{18}$ or together are —$(CH_2)_2$-Z-$(CH_2)_2$—. The group $R^{18}$ is OH, a phenyl group or an aromatic heterocycle selected from pyridyl, pyrimidinyl, pyrazinyl, furyl, thienyl, pyrrolyl, imidazolyl, pyrazolyl, oxazolyl, isoxazolyl, thiazolyl, isothiazolyl, triazolyl, oxadiazolyl and thiadiazolyl, each of which may optionally have a lower alkyl group or lower alkenyl group substituent. Z is selected from O, $CH_2$, S, $SO_2$, NH, N-lower alkyl and N-lower alkenyl.

In further aspects, the present invention comprises a pharmaceutical composition wherein one of the active agents is a compound according to general formula 1, the use of a compound according to general formula 1 for the preparation of such a pharmaceutical composition, and methods of treatment of certain medical conditions.

DETAILED DESCRIPTION OF THE INVENTION

In a first aspect, the present invention comprises compounds which are derivatives according to general formula 1.

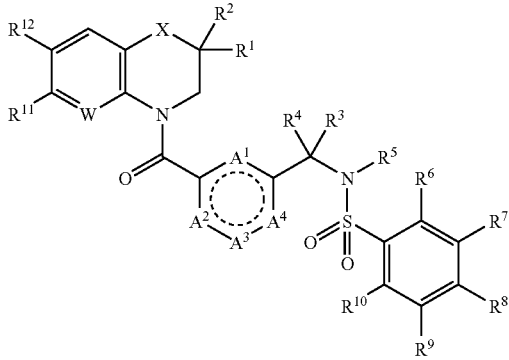

1

The ring including $A^1$-$A^4$ is a five- or six-membered carbocyclic or heterocyclic group. The dotted circle within this group is intended to indicate that the ring incorporates the appropriate number of double and single bonds for an aromatic ring of the corresponding size, namely two double bonds and three single bonds for a five-membered ring, and three double bonds and three single bonds for a six-membered ring. Subject to certain provisions depending on the nature of $A^4$, $A^1$-$A^3$ each may be selected from $A^5$ and $A^6$, where $A^5$ may be either =$CR^{13}$— or =N— and $A^6$ may be —$NR^{14}$—, —O— or —S—. $A^4$ may be either a covalent bond or $A^5$. When $A^4$ is a covalent bond, such that the ring including $A^1$-$A^4$ is a five-membered ring, one of $A^1$-$A^3$ must be $A^6$ and the other two must be $A^5$. When $A^4$ is $A^5$ such that the ring is a six-membered ring, then all of $A^1$-$A^3$ must be $A^5$. These restrictions allow for the ring to have one of the following four part-structures.

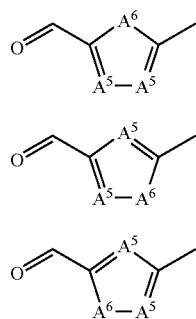

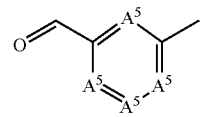

5

For part structures 2-4 the two groups represented by $A^5$ are independent of each other, so that both may be =N— or =$CR^{13}$—, or one may be =N— and the other =$CR^{13}$—. Similarly, in part-structure 5, the four groups represented by $A^5$ are independent, so that all may be =N—, all =$CR^{13}$—, or between one and three may be =N— and the rest =$CR^{13}$—. Furthermore, when a compound has more than one occurrence of =$CR^{13}$—, the value of $R^{13}$ for each occurrence is independent of the others. In all cases, the 1,3-relationship between the carbonyl and aminomethyl substituents is preserved.

The group $R^1$ may be selected from H (a hydrogen atom), $NHY^1$ and $COY^2$. In any of these cases the group $R^2$ is H. Alternatively, $R^1$ and $R^2$ may both be methyl or together may represent =O so as to form a carbonyl group.

The groups $R^3$, $R^4$ and $R^5$ are each independently selected from H, lower alkyl and lower alkenyl groups.

The groups $R^6$, $R^7$, $R^8$, $R^9$, $R^{10}$, $R^{11}$ and $R^{12}$ are each independently selected from H, lower alkyl and lower alkenyl groups, $NH_2$, halogens (F, Cl and Br) O-alkyl, $CH_2NMe_2$ and $CF_3$.

The group $R^{13}$ is selected from H, F, Cl, Br, $NO_2$, $NH_2$, OH, Me, Et, OMe, $NMe_2$ and $CF_3$.

The group $R^{14}$ is selected from H, methyl and ethyl.

W is selected from =CH— and =N—.

X is selected from $CH_2$, O, S, $SO_2$, NH, N-lower alkyl and N-lower alkenyl.

The group $Y^1$ is selected from CO-lower alkyl, CO-lower alkenyl, $CO(CH_2)_bY^3$, $CO(CH_2)_bCOY^3$ and $CO(CH_2)_b$NH-$COY^3$, where b is 1-3.

The group $Y^2$ is selected from $OR^{15}$, $NR^{16}R^{17}$ and $NH(CH_2)_cCOY^3$, where c is 1-3.

The group $Y^3$ is selected from lower alkyl, lower alkenyl, $OR^{15}$ and $NR^{16}R^{17}$.

The group $R^{15}$ is selected from H, lower alkyl, lower alkenyl, and $(CH_2)_aR^{18}$ where a is 0-4.

The groups $R^{16}$ and $R^{17}$ are each independently selected from H, lower alkyl, lower alkenyl and $(CH_2)_aR^{18}$, or together are —$(CH_2)_2$-Z-$(CH_2)_2$—.

The group $R^{18}$ is OH, a phenyl group or an aromatic heterocycle selected from pyridyl, pyrimidinyl, pyrazinyl, furyl, thienyl, pyrrolyl, imidazolyl, pyrazolyl, oxazolyl, isoxazolyl, thiazolyl, isothiazolyl, triazolyl, oxadiazolyl and thiadiazolyl, each of which may optionally have a lower alkyl or lower alkenyl group substituent.

Z is selected from O, $CH_2$, S, $SO_2$, NH, N-lower alkyl and N-lower alkenyl groups.

In the context of the present specification, lower alkyl groups include linear, branched and cyclic alkyl groups of up to six carbon atoms, including, but not limited to, methyl, ethyl, propyl, isopropyl, butyl, isobutyl, tert-butyl, pentyl, tert-amyl, neopentyl, cyclopropyl, cyclohexyl, cyclopropylmethyl, and the like. Lower alkenyl groups include monounsaturated linear, branched and cyclic alkenyl groups of up to six carbons, including, but not limited to, allyl, but-2-enyl, cyclopent-3-enyl and the like. Alkenyl groups wherein the double bond is at the point of attachment, such as vinyl and 1-propenyl, are not considered to be lower alkenyl groups in the context of the present specification.

Certain compounds according to general formula 1 are capable of forming salts with acids or bases. For example, compounds according to general formula 1 which have an acidic functional group may be capable of forming sodium, potassium, calcium, magnesium or tetraalkylammonium salts upon treatment with the corresponding hydroxide, carbonate or bicarbonate, or of forming trialkylammonium salts upon reaction with the corresponding amine. Alternatively, compounds according to general formula 1 which have a basic group may be capable of forming addition salts with inorganic and organic acids such as hydrochloric acid, sulphuric acid, phosphoric acid, acetic acid, trifluoroacetic acid, benzoic acid, pamoic acid, citric acid, fumaric acid, methanesulphonic acid and the like. To the extent that such salts are pharmaceutically acceptable, they are considered to be included within the scope of the present invention.

The compounds according to general formula 1 may include one or more stereogenic ("asymmetric") centres. Such compounds exhibit optical isomerism, and so can exist as enantiomers or diastereomers. Such isomers, either alone or as mixtures, including but not limited to racemic mixtures, are also considered to be within the scope of the present invention.

In a preferred embodiment, the present invention comprises a compound according to general formula 1 wherein $R^3$ and $R^4$ are both H.

In another preferred embodiment, the present invention comprises a compound according to general formula 1 wherein $R^5$ is a lower alkyl or lower alkenyl group, and more preferably a methyl group.

In another preferred embodiment, the present invention comprises a compound according to general formula 1 wherein $A^1$, $A^2$, $A^3$ and $A^4$ are all $A^5$. More preferably, they are all $=CR^{13}—$ or three are $=CR^{13}—$ and one is $=N—$. More preferably still, $A^1$, $A^3$ and $A^4$ are $=CH—$ and $A^2$ is $=CR^{13}—$. Most preferably, $A^1$, $A^3$ and $A^4$ are $=CH—$ and $A^2$ is $=CF—$ or $=CCl—$. In an alternative more preferred embodiment, one of $A^1$, $A^2$, $A^3$ and $A^4$ is $=N—$ and the others are $=CH—$. Most preferably, $A^1$ is $=N—$ and $A^2$, $A^3$ and $A^4$ are $=CH—$.

In another preferred embodiment, the present invention comprises a compound according to general formula 1 wherein $A^4$ is a covalent bond. More preferably, $A^1$ and one of $A^2$ and $A^3$ are $A^5$, with the other being $A^6$. Most preferably, $A^1$ is $A^5$, one of $A^2$ and $A^3$ is $=CH—$ and the other is $—S—$.

In another preferred embodiment, the present invention comprises a compound according to general formula 1 wherein at least three of $R^6$-$R^{10}$ are H. More preferably, four of $R^6$-$R^{10}$ are H and one is halogen or trifluoromethyl. Most preferably, $R^6$, $R^7$, $R^9$ and $R^{10}$ are H and $R^8$ is halogen or trifluoromethyl.

In another preferred embodiment, the present invention comprises a compound according to general formula 1 wherein $R^1$ is $COY^2$ and $R^2$ is H. More preferably, $Y^2$ is $NR^{16}R^{17}$ or $NHCH_2COY^3$. Most preferably, $Y^2$ is $NH—CH_2—R^{18}$ or $NHCH_2CONHCH_3$, where $R^{18}$ is pyridyl or 3-methyl-1,2,4-oxadiazol-5-yl.

The compounds according to general formula 1 can be prepared by two routes, as outlined in the following Scheme.

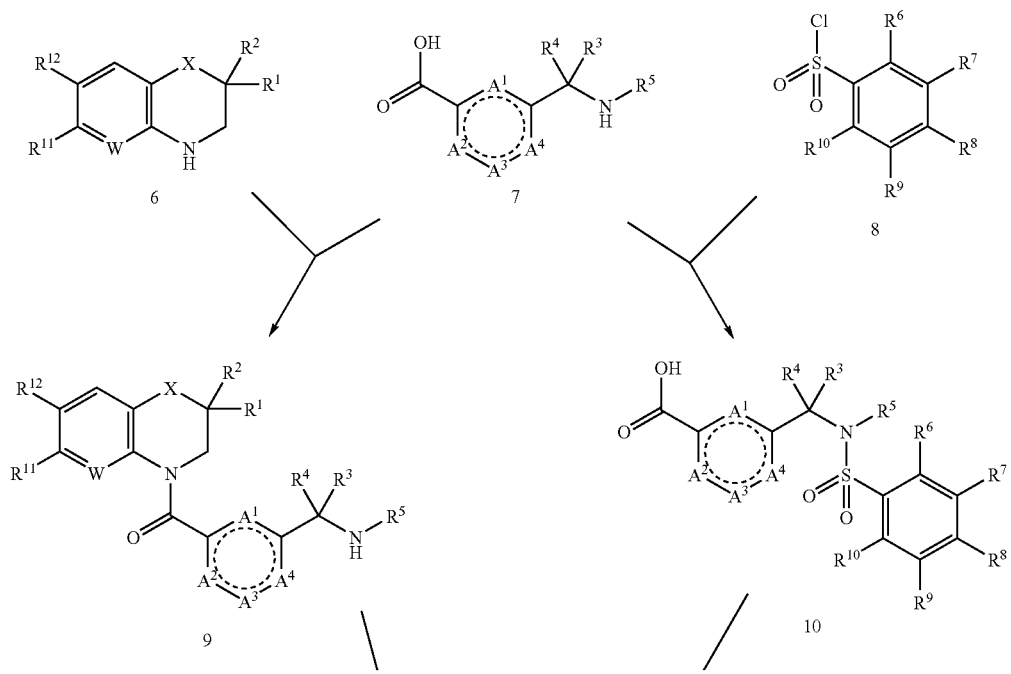

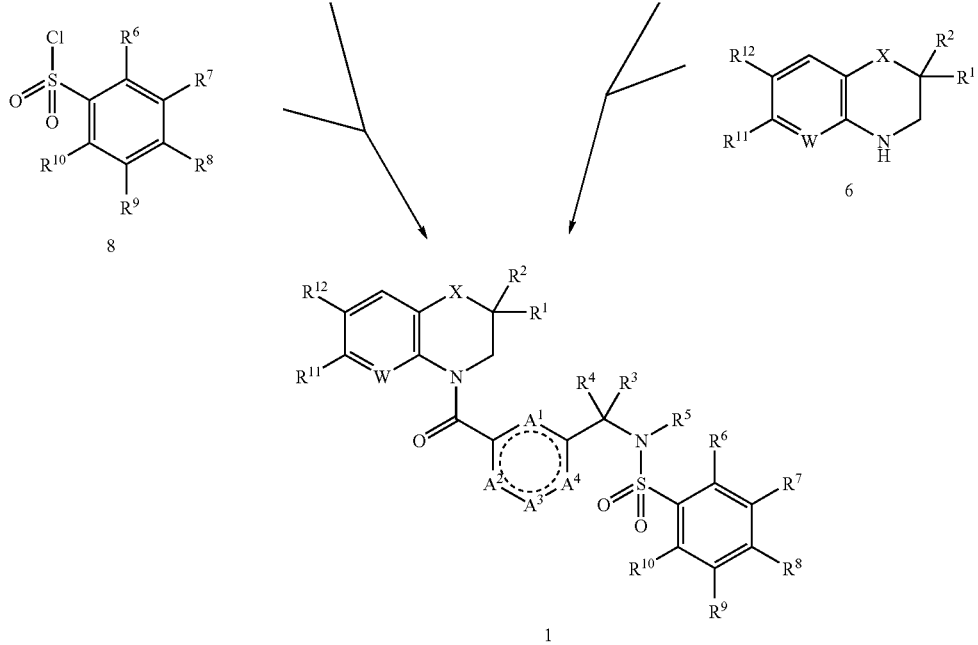

-continued

Three starting materials, corresponding to general formulae 6, 7 and 8 are required. Either 6 and 7 are combined to give an intermediate of general formula 9, or 7 and 8 are combined to give an intermediate of general formula 10. Thereafter, either 8 and 9 or 6 and 10 are combined to give the product of general formula 1. In order to avoid side-reactions, it will usually be necessary to employ appropriate protecting groups during certain stages of the synthesis. The use of such protecting groups is well known in the art. For example, see Greene, T W; "*Protective Groups in Organic Synthesis*", Wiley, New York 1999. In particular, the amino group of starting material 7 is likely to be incompatible with the conditions required to effect the reaction of 6 with 7 and so will need to be protected. Suitable protecting groups are, for example, tert-butyloxycarbonyl (Boc) and benzyloxycarbonyl (Z) groups. The carboxylic acid group of 7 may also require protection. If so, it may be protected as an ester such as the methyl, ethyl, tert-butyl or benzyl ester.

It will be apparent from the Scheme that the two synthetic strategies require the same chemical transformations and differ only in the order in which these are carried out. The two transformations are:

i formation of an amide from a carboxylic acid and a cyclic amine (6+7→9; 6+10→1); and
ii formation of a sulphonamide from a sulphonyl chloride and an amine (7+8→10; 8+9→1).

The formation of an amide is a well known operation. The carboxylic acid and the amine are mixed in an appropriate solvent, which is generally an aprotic solvent such as dichloromethane or dimethylformamide, and a condensing agent is added. A large number of such agents are now available. Suitable agents include carbodiimides such as dicyclohexylcarbodiimide (DCC), diisopropylcarbodiimide (DIC), and N-(dimethylamino-propyl)-N'-(ethyl)-carbodiimide (water-soluble carbodiimide, WSC.HCl, phosphorus derivatives such as (benzotriazol-1-yloxy)tris(dimethylamino)phosphonium hexafluorophosphate (BOP), (benzotriazol-1-yloxy)tripyrrolidinophosphonium hexafluorophosphate (PyBOPtrademark) and bis(2-oxo-3-oxazolidinyl) phosphinic chloride (BOP-Cl), and urea derivatives such as O-(benzotriazol-1-yl)-N,N,N',N'-tetramethyluronium hexafluorophosphate (HBTU). A tertiary amine may also be included in the reaction mixture. Examples of such tertiary amines include triethylamine, diisopropylethylamine and 4-dimethylaminopyridine. The reaction is generally carried out at room temperature or at a lower temperature such as 0° C. or −20° C. In cases where the reaction is slow, it is also possible to warm the mixture to a temperature not greater than the boiling point of the solvent.

The formation of a sulphonamide is also a well known operation. Generally, the sulphonyl chloride and the amine are mixed in an aprotic solvent such as dichloromethane or dimethylformamide in the presence of a tertiary amine (for example triethylamine, diisopropylethylamine and 4-dimethylaminopyridine). There is no need to add a condensing agent. The reaction is generally performed at around room temperature.

The starting materials (6, 7 and 8) are prepared according to published methods, or by modifications to these methods. In some cases it may be necessary or desirable to carry out final modifications to the molecule after the three components have been assembled. Such extensions and modifications will be obvious to those familiar with the art.

The compounds according to general formula 1 are potent and specific antagonists of the GnRH receptor. Therefore they are useful in the treatment of conditions wherein GnRH is implicated in the pathophysiology. For example, the compounds can be used in the treatment of certain hormone-dependent cancers, such as cancer of the breast or of the prostate. They may also be used to treat non-cancerous conditions such as benign prostate hyperplasia and endometriosis. Because of their ability to block the release of LH and FSH, the compounds can be used to regulate fertility. They can be used as contraceptive agents in either male or female subjects. They can also be used in assisted fertilisation programs where K is necessary to control the levels of circulating hormones in order to optimise the chances of obtaining mature ova. They may also be used in the management of criminal anti-social behaviour.

In a second aspect, therefore, the present invention comprises a use for a compound of general formula 1, which use is as a therapeutic agent in human or animal medicine. When employed for this purpose, the compound will be formulated and administered as is generally known in the art, and as further described below.

In a preferred embodiment, the compound is used as in the treatment of a hormone-dependent cancer, benign prostate hyperplasia, or endometriosis, as a contraceptive agent, as an adjunct to an assisted fertilisation program, or as a behaviour-modifying agent. In another preferred embodiment, the compound is used in human medicine.

In a third aspect, the present invention comprises a pharmaceutical composition which is characterised in that it includes at least one compound according to general formula 1 as an active agent. The composition may be a solid, such as a tablet, capsule, powder, suppository or the like, or a liquid, such as a solution, suspension, emulsion or cream. The composition may include such excipients as are generally known in the art, including bulking agents, binding agents, diluents, dispersents, lubricants, solvents, preservatives and flavouring agents.

In a preferred embodiment, the composition is a tablet or capsule suitable for oral administration.

In another preferred embodiment, the composition is intended for the treatment of a hormone-dependent cancer, benign prostate hyperplasia, or endometriosis, as a contraceptive agent, as an adjunct to an assisted fertilisation program, or as a behaviour-modifying agent.

In a fourth aspect, the present invention comprises a use for a compound according to general formula 1, which use is as a component of a pharmaceutical composition.

In a fifth aspect, the present invention comprises a new method of treatment in human or animal medicine, which method is characterised in that a therapeutically effective amount of a compound according to general formula 1 is administered to the subject in order to bring about the desired outcome.

The compound, when formulated as an appropriate pharmaceutical composition, may be administered by any suitable route, including oral, buccal, nasal, pulmonary, rectal, vaginal, transdermal, intramuscular, subcutaneous and intravenous administration. The amount administered, and the frequency with which the administration is repeated, will be determined by the attending physician (or veterinarian), taking in to account the condition and medical history of the subject and the therapeutic outcome desired. A typical human dose will be in the range of 0.1 mg to 500 mg. The dose may be administered once per day or up to four times per day. The course of treatment may involve a single administration or repeated administration for a period of a few days or weeks up to several years when the condition being treated is chronic.

In a preferred embodiment, the subject is a human male or female.

In another preferred embodiment, the condition being treated is a hormone-dependent cancer. More preferably, it is prostate cancer or breast cancer.

In another preferred embodiment, the condition being treated is endometriosis.

In another preferred embodiment, the condition being treated is benign prostate hyperplasia.

In another preferred embodiment, the condition being treated is infertility. In particular, the treatment is part of a program of assisted fertilisation.

In another preferred embodiment, the aim of the treatment is to provide contraception.

In another preferred embodiment, the subject is a "sex offender", i.e. the subject has committed sexual attacks on other people.

The present invention, as described above, is further described by means of the following Examples, which are intended to be illustrative of the invention rather than limiting in any way the scope of the invention.

EXAMPLES

Chromatography refers to "flash" chromatography on silica gel unless otherwise stated.

A. Synthesis of Intermediates

Benzomorpholine

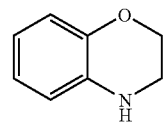

2H-1,4-benzoxazin-3-(4M-one (4.5 g, 30 mmol) was added portionwise to a stirred suspension of lithium aluminium hydride (4.7 g, 120 mmol) in THF (100 ml) and heated at reflux for 3 h. The mixture was cooled in an ice/water bath and ammonia solution (8 ml) and water (40 ml) were added while stirring. The mixture was filtered through Celite and reduced. Chromatography (50% EtOAc/ 50% 60-80 petroleum ether) afforded benzomorpholine (3.7 g, 91%) as a pale brown oil.

Pyrrido[3,2-b]morpholine

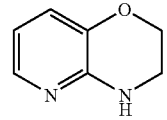

2H-pyrido[3,2-b]-1,4-oxazin-3-(4H)-one (1.9 g, 12.6 mmol) was added to a suspension of lithium aluminium hydride (2.0 g, 53 mmol) in dry THF (100 ml) while cooling in an ice/water bath. The mixture was warmed to 60° C. and stirred for 4 h. The mixture was cooled again in an ice/water bath and water (20 ml) was added slowly, followed by ethyl acetate (200 ml). The mixture was filtered and separated. The organic phase was washed with water and brine, dried and reduced to afford pyrrido[3,2-b]morpholine (1.5 g, 89%) as a white solid.

Ethyl benzomorpholine-2-carboxylate

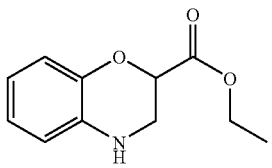

Ethyl 2,3-dibromopropionate (24 g, 92 mmol) was added dropwise to a refluxing solution of o-aminophenol (10 g, 92 mmol) and potassium carbonate (15 g, 110 mmol) in acetone (100 ml). After 18 h the mixture was cooled and reduced. Ethyl acetate and water were added and the mixture separated. The organic phase was washed with brine, filtered and reduced. Chromatography (30% EtOAc/70% 60-80 petroleum ether) afforded ethyl benzomorpholine-2-carboxylate (4.5 g, 24%) as a red oil.

Benzomorpholine-2-carboxylic acid

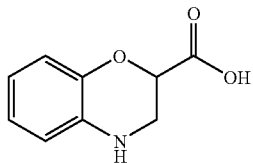

A solution of lithium hydroxide (290 ml, 7.0 mmol) in water (10 ml) was added to a solution of ethyl benzomorpholine-2-carboxylate (750 mg, 3.6 mmol) in dioxan (15 ml). The mixture was stirred for 18 h and reduced to afford benzomorpholine-2-carboxylic acid as its lithium salt, which was used without further purification.

1,2,3,4-Tetrahydroquinoxalin-2-one

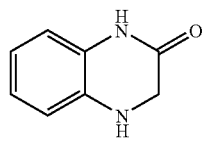

a) Glycine methyl ester hydrochloride (2.2 g, 18 mmol), diisopropylethylamine (2.9 g, 29 mmol), 18-crown-6 (370 mg, 1.4 mmol) and potassium fluoride (1.6 g, 28 mmol) were added to a solution of 1-fluoro-2-nitrobenzene (2 g, 14 mmol) in acetonitrile (150 ml). The mixture was heated at 80° C. for 48 h and cooled. 0.3N potassium hydrogen sulphate and ethyl acetate were added and the mixture separated. The organic phase was washed with water and brine, filtered through phase separation paper and reduced. Chromatography (15% EtOAc/85% 6080 petroleum ether) afforded N-(2-nitrophenyl)glycine methyl ester as a yellow solid (2.5 g, 85%).

b) A solution of N-(2-nitrophenyl)glycine methyl ester (740 mg, 3.6 mmol) in ethyl acetate (50 ml) and methanol (25 ml) was hydrogenated at atmospheric pressure over a catalytic amount of 10% palladium on carbon. After 1 h the mixture was filtered and reduced to afford 1,2,3,4-tetrahydroquinoxalin-2-one as a yellow solid (530 mg, 99%).

3-Acetamido-1,2,3,4-tetrahydroquinoline

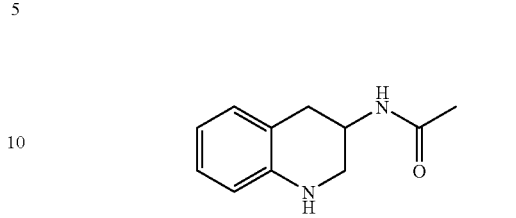

a) Acetyl chloride (410 mg, 5.2 mmol) and triethylamine (620 mg, 6.2 mmol) were added to a solution of 3-aminoquinoline (710 mg, 4.9 mmol) in dichloromethane (50 ml) and the mixture was stirred at room temperature for 18 h. Chloroform (100 ml) was added, the mixture acidified with 1N hydrochloric acid (50 ml) and the phases separated. The aqueous phase was basified with 1N sodium hydroxide solution and extracted with chloroform/IPA (85:15, 175 ml). The organic extract was washed with water, brine, dried and reduced to afford 3-acetamidoquinoline (780 mg, 84%) as a yellow solid.

b) Borane-pyridine complex (320 mg, 3.5 mmol) was added to a solution of 3-acetamidoquinoline (320 mg, 1.7 mmol) in acetic acid (20 ml) and the mixture was stirred at room temperature for 18 h. Chloroform (150 ml) was added and the mixture was washed with 2N sodium hydroxide solution, water and brine. The organic phase was dried and reduced. Chromatography (80% EtOAc/20% 60-80 pet. ether) afforded 3-acetamido-1,2,3,4-tetrahydroquinoline (180 mg, 55%) as a pale yellow solid.

N-(2-Hydroxyethyl)benzomorpholine-2-carboxamide

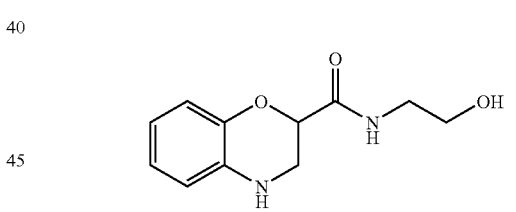

HOBT (3.1 g, 20 mmol) was added to a solution of lithium benzomorpholine-2-carboxylate (2.6 g, 15 mmol) in dichloromethane (75 ml) and DMF (7.0 ml) and cooled in an ice/water bath. WSC.HCl (3.2 g, 17 mmol) was added, the mixture was allowed to warm to room temperature and stirred for 1 h. The mixture was cooled in an ice/water bath again and ethanolamine (1.0 g, 17 mmol) and triethylamine (2.8 ml, 2.0 g, 20 mmol) were added.

Stirring was continued at room temperature for 3 days. The mixture was reduced and taken up in ethyl acetate and 0.3N potassium hydrogen sulphate solution. The phases were separated. The organic phase was washed with saturated sodium hydrogen carbonate solution and the aqueous phase was back-extracted with ethyl acetate and chloroform. The combined organic phases were dried and reduced. Chromatography (6% methanol/94% chloroform) afforded N-(2-hydroxyethyl)benzomorpholine-2-carboxamide (1.19 g 33%) as a brown gum.

N-(3-Methyl-1,2,4-oxadiazol-5-ylmethyl)benzomorpholine-2-carboxamide

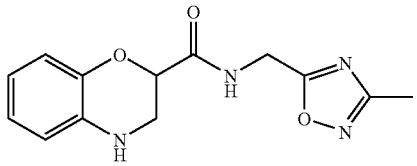

HOBT (1.0 g, 6.5 mmol) and WSC.HCl (1.1 g, 5.8 mmol) were added to a solution of lithium benzomorpholine-2-carboxylate (900 mg, 5.0 mmol) in dichloromethane (25 ml) and DMF (4.0 ml) while cooling in an ice/water bath. The mixture was allowed to warm to room temperature and stirred for 45 min. Triethylamine (0.73 ml, 530 mg, 5.2 mmol) and a solution of 3-methyl-1,2,4-oxadiazol-5-ylmethylamine (590 mg, 5.2 mmol, prepared according to H. Biere et al., *Liebigs Ann. Chem.* 1749 (1986)) in dichloromethane (5.0 ml) were added and the mixture was stirred for 18 h. The mixture was reduced, taken up in ethyl acetate and washed with 0.3N potassium hydrogen sulphate, saturated sodium hydrogen carbonate and brine. The organic phase was dried and reduced. Chromatography (80% ethyl acetate/20% 60-80 petroleum ether) afforded N-(3-methyl-1,2,4-oxadiazol-5-ylmethyl)benzomorpholine-2-carboxamide (900 mg, 65%) as a brown gum.

tert-Butyl N-(3-chloro-2-(methyloxycarbonyl)thiophene-4-methyl)-N-methylcarbamate

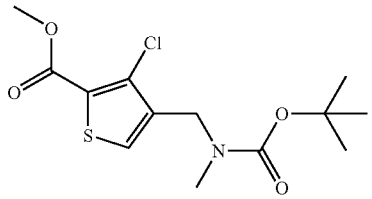

a) A solution of methyl 3-chloro-4-methylthiophenecarboxylate (10 g, 53 mmol), N-bromosuccinimide (9.4 g, 53 mmol) and azo-bis-(isobutyronitrile) (860 mg, 5.3 mmol) in carbon tetrachloride (300 ml) was heated at reflux for 18 h. The mixture was filtered and reduced. Chromatography (10% EtOAc/90% hexanes) afforded methyl 4-bromomethyl-3-chlorothiophene-2-carboxylate (5.5 g, 39%) as a white solid.

b) A solution of methyl 4-bromomethyl-3-chlorothiophene-2-carboxylate (7.6 g, 28 mmol) in saturated ammonia/ethanol (200 ml) was stirred at room temperature for 18 h. The mixture was reduced in vacuo, triturated in ether and taken up in dioxan (200 ml). Sodium hydroxide (3.4 g, 85 mmol), di-tert-butyl dicarbonate (9.2 g, 42 mmol) and water (200 ml) were added and the mixture stirred for 18 h. Excess sodium hydroxide was added and the mixture heated at 70° C. for 3 h. The mixture was washed with diethyl ether and acidified with solid potassium hydrogen sulphate. The mixture was extracted with ethyl acetate and dichloromethane, dried and reduced to afford tert-butyl N-(3-chloro-2-carboxythiophene-4-methyl)carbamate (6.0 g, 73%) as a brown oil.

c) Sodium hydride (60% dispersion, 820 mg, 21 mmol) was added to a solution of tert-butyl N-(3-chloro-2-carboxythiophenemethyl)carbamate (2.0 g, 6.8 mmol) in DMF (30 ml) while cooling in an ice/water bath. The mixture was allowed to warm to room temperature over 1 h. Iodomethane (4.0 ml) was added and the mixture was stirred for 18 h. Water was added and the mixture was acidified with dilute potassium hydrogen sulphate solution and extracted with EtOAc. The organic phase was washed with water and brine, dried and reduced. Chromatography (20% EtOAC. 80% hexanes) afforded tert-butyl N-(3-chloro-2-(methyloxycarbonyl)thiophene-4-methyl)-N-methylcarbamate (1.52 g, 70%) as a brown oil.

Ethyl 2-(methylaminomethyl)thiazole-4-carboxylate

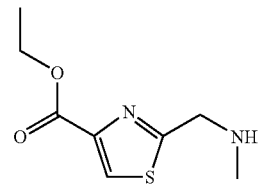

a) A solution of ethyl 2-methylthiazole-4-carboxylate (5.0 g, 29 mmol), N-bromosuccinimide (6.2 g, 35 mmol) and azo-bis-(isobutyronitrile) (480 mg, 2.9 mmol) in carbon tetrachloride (150 ml) was heated at reflux for 18 h. The mixture was filtered and reduced. Chromatography (20% EtOAc/80% hexanes and 30% EtOAc/70% hexanes) afforded ethyl 2-bromomethylthiazole-4-carboxylate (3.25 g, 44%).

b) A solution of ethyl 2-bromomethylthiazole-4-carboxylate (4.25 g, 17 mmol) in THF (50 ml) was added to a solution of methylamine in THF (2M, 30 ml, 60 mmol) drop-wise while cooling to −10° C. The mixture was allowed to warm to room temperature and stirred for a further 30 min. The mixture was diluted with EtOAc and washed with 0.3N potassium hydrogen sulphate solution and brine. The organic phase was dried and reduced to yield ethyl 2-(methylaminomethyl)thiazole-4-carboxylate (3.06 g, 70%) as an orange oil which was used without further purification.

tert-Butyl N-methyl-N-(3-(methyloxycarbonyl)benzyl)carbamate

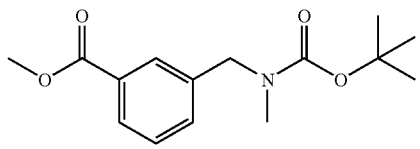

a) A mixture of 3-cyanobenzoic acid (5.0 g, 34 mmol), 10% palladium on carbon (1 g) and concentrated hydrochloric acid (3 ml) in methanol (150 ml) was stirred under hydrogen gas at atmospheric pressure for 6 h. The mixture was filtered through Celite®, reduced and azeotroped with toluene. The residue was taken up in 1M potassium hydrogen carbonate solution (105 ml) and dioxan (50 ml) and cooled in an ice/water bath. A solution of di-tert-butyl dicarbonate (7.9 g, 36 mmol) in dioxan (25 ml) was added and the mixture was allowed to warm to room temperature. After stirring for 3 days the dioxan was removed in vacuo. The aqueous residue was washed with 60-80 pet.ether, acidified with 1N hydrochloric acid and extracted with ethyl acetate. The organic phase was washed with brine, dried and reduced to afford tert-butyl N-(3-carboxybenzyl)carbamate (8.2 g, 86%) as a white solid.

b) Sodium hydride (60% dispersion, 700 mg, 18 mmol) was added to a solution of tert-butyl N-(3-carboxybenzyl)carbamate (2.0 g, 8.0 mmol) in DMF (40 ml) while cooling in an ice/water bath. After 15 min the mixture was allowed to warm to room temperature for 15 min. The mixture was cooled again in an ice/water bath and iodomethane (3.7 ml, 8.4 g, 60 mmol) was added. The mixture was stirred at room temperature for 18 h. Water was added and the mixture was concentrated in vacuo. Ethyl acetate and 0.3N potassium hydrogen sulphate were added and the mixture separated. The organic phase was washed with brine, dried and reduced. Chromatography (20% EtOAc, 80% 60-80 pet.ether) afforded tert-butyl N-methyl-N-(3-(methyloxycarbonyl)benzyl)carbamate (1.6 g, 69%) as a colourless oil.

tert-Butyl N-(3-carboxybenzyl)-N-methylcarbamate

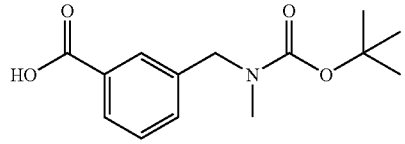

Lithium hydroxide monohydrate (420 mg, 10 mmol) and water (15 ml) were added to a solution of tert-butyl N-methyl-N-(3-(methyloxycarbonyl)benzyl)carbamate (1.6 g, 5.6 mmol) in dioxan (20 ml) and the mixture was stirred for 2 h. The dioxan was removed in vacuo and the residue was taken up in 0.3N potassium hydrogen sulphate. The mixture was extracted with ethyl acetate and the organic phase was washed with water and brine, dried and reduced to afford tert-butyl N-(3-carboxybenzyl)-N-methylcarbamate (1.4 g, 95%).

tert-Butyl(1-(4-carboxythiazol-2-yl)ethyl)carbamate

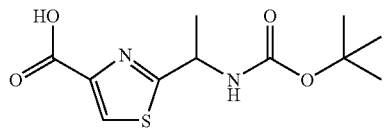

a) Potassium hydrogen carbonate (1.58 g, 15.7 mmol) and ethyl bromopyruvate (2.1 ml, 16.9 mmol) were added to a solution of (R,S)-2-(tert-butyloxycarbonylamino)-thiopropionamide (800 mg, 3.9 mmol) in 1,2-dimethoxyethane (10 ml) at −10° C. The mixture was stirred and allowed to warm to 0° C. over 2 h and to room temperature over 1.5 h. The mixture was filtered and the solid washed with diethyl ether. The filtrate was concentrated, taken up in 1,2-dimethoxyethane (10 ml) and cooled to −30° C. To this solution was added trifluoroacetic anhydride (1.8 ml, 12.8 mmol) and 2,6-lutidine (3.2 ml, 27.2 mmol). After 50 min the solution was concentrated and partitioned between chloroform and water. The organic layer was dried and concentrated to afford tert-butyl(1-(4-(ethyloxycarbonyl)thiazol-2-yl)ethyl)carbamate (1.4 g) as crude material that was used directly in the next step.

b) Lithium hydroxide monohydrate (165 mg, 3.9 mmol) was added to a solution of tert-butyl (1-(4-(ethyloxycarbonyl)thiazol-2-yl)ethyl)carbamate (1.4 g crude material) in THF (25 ml) and water (20 ml) and stirred at room temperature for 18 h. A further amount of lithium hydroxide monohydrate was added (165 mg) and stirring continued for 4 h. The THF was removed in vacuo, the aqueous residue acidified with 1N hydrochloric acid and extracted twice with chloroform. The combined organic layers were washed with brine, dried and reduced. Chromatography (50:2:1 chloroform, methanol, acetic acid) and recrystallisation (EtOAc/hexanes) afforded tert-butyl(1-(4-carboxythiazol-2-yl)ethyl)carbamate (686 mg, 64% over two steps).

B. Synthesis of Compounds of the Invention

Example 1

4-Bromo-N-methyl-N-(3-(1,2,3,4-tetrahydroquinoline-1-carbonyl)benzyl)benzenesulphonamide

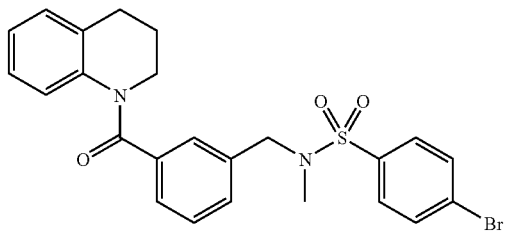

a) 1,2,3,4-tetrahydroquinoline (4.2 g, 31 mmol) was added dropwise to a solution of 3-cyanobenzoyl chloride (5.2 g, 31 mmol) and triethylamine (3.1 g, 31 mmol) in dichloromethane (125 ml) while cooling in an ice/water bath. The mixture was allowed to warm to RT and stirred for 18 h. It was washed with 0.3M potassium hydrogen sulphate solution, saturated sodium hydrogen carbonate solution and brine. The organic phase was filtered through phase separation paper and reduced to yield 1-(3-cyanobenzoyl)-1,2,3,4-tetrahydroquinoline (7.1 g, 86%).

b) A solution of 1-(3-cyanobenzoyl)-1,2,3,4-tetrahydroquinoline (7.1 g, 27 mmol) and hydrochloric acid (2.2 ml) in methanol (100 ml) was hydrogenated at atmospheric pressure for 8 h over a catalytic amount of 10% palladium on carbon. The mixture was filtered through Celite® and reduced to yield 1-(3-aminomethylbenzoyl)-1,2,3,4-tetrahydroquinoline hydrochloride (8.1 g, 99%) as a white solid.

c) Di-tert-butyl dicarbonate (7.1 g, 32 mmol) was added to a solution of 1-(3-aminomethylbenzoyl)-1,2,3,4-tetrahydroquinoline hydrochloride (8.1 g, 27 mmol) and triethylamine (7.5 ml, 54 mmol) in dichloromethane (200 ml) and stirred for 18 h. The mixture was washed with 0.3M potassium hydrogen sulphate solution, water, sodium hydrogen carbonate solution and brine. The organic phase was dried over sodium sulphate, filtered through phase separation paper and reduced. Chromatography (silica gel, 30% EtOAc, 70% 40-60 petroleum ether) afforded tert-butyl N-(3-(1,2,3,4-tetrahydroquinoline-1-carbonyl)benzyl)carbamate (8.0 g, 84%) as a white solid.

d) Sodium hydride (0.91 g, 60% dispersion in oil, 23 mmol) was added to a solution of tert-butyl N-(3-(1,2,3,4- tetrahydroquinoline-1-carbonyl)benzyl)carbamate (8.0 g, 22 mmol) in DMF under nitrogen, while cooling in an ice/water bath. Allowed to warm to room temperature over 45 min. The mixture was cooled in an ice/water bath and iodomethane (9.8 g, 68 mmol) was added dropwise. Allowed to warm to room temperatue and stirred for 5 h. 0.3N Potassium hydrogen sulphate was added and the mixture was extracted with EtOAc. The organic phase was washed with water, dried over sodium sulphate and evaporated. Chromatography (30% EtOAc, 70% 60-80 petroleum ether) afforded tert-butyl N-methyl-N-(3-(1,2,3,4-tetrahydroquinoline-1-carbonyl)benzyl)carbamate (7.7 g, 93%) as a yellow gum.

e) A solution of tert-butyl N-methyl-N-(3-(1,2,3,4-tetrahydroquinoline-1-carbonyl)benzyl)-carbamate (7.7 g, 20 mmol) in 4N hydrogen chloride/dioxan solution (20 ml) was stirred for 30 min. The mixture was reduced and azeotroped with toluene and dichloromethane to yield 1-(3-methylaminomethylbenzoyl)-1,2,3,4-tetrahydroquinoline hydrochloride as a glass (6.3 g, 99%).

f) 1-(3-Methylaminomethylbenzoyl)-1,2,3,4-tetrahydroquinoline free base was isolated by aqueous work-up of the HCl salt with saturated sodium hydrogen carbonate solution, extraction with dichloromethane and reduction in vacuo. 4-Bromobenzenesulphonyl chloride (41 mg, 0.16 mmol) was added to a solution of the free base (42 mg, 0.15 mmol) and triethylamine (30 µl, 0.20 mmol) in dichloromethane (10 ml) and stirred for 3 h. The mixture was evaporated and chromatographed (35% EtOAc/65% 60-80 pet ether) to afford 4-bromo-N-methyl-N-(3-(1,2,3,4-tetrahydroquinoline-1-carbonyl)benzyl)benzenesulphonamide as a white solid (40 mg, 53%).

$^1$H NMR (CDCl$_3$), 1.88-2.08 (2H, m), 2.35 (3H, s), 2.65-2.75 (2H, m), 3.70-3.90 (2H, m), 3.95 (2H, s), 6.55-6.62 (1H, m), 6.75 (1H, t, J=8 Hz), 6.90 (1H, t, J=8 Hz), 7.05-7.15 (2H, m), 7.20-7.35 (3H, m), 7.50-7.65 (4H, m). ESIMS m/z=499.4, 501.4 (50:50, MH$^+$). Microanalysis; Found: C, 57.79%; H, 4.69%; N, 5.76%; Calc. for C$_{24}$H$_{23}$BrN$_2$O$_3$S: C, 57.72%; H, 4.64%; N, 5.61%.

Example 2

4-(3-Chloro-4-N-(4-chlorobenzenesulphonyl)-N-methylaminomethyl)thiophene-2-carbonyl)-N-(3-methyl-1,2,4-oxadiazol-5-ylmethyl)benzomorpholine-2-carboxamide

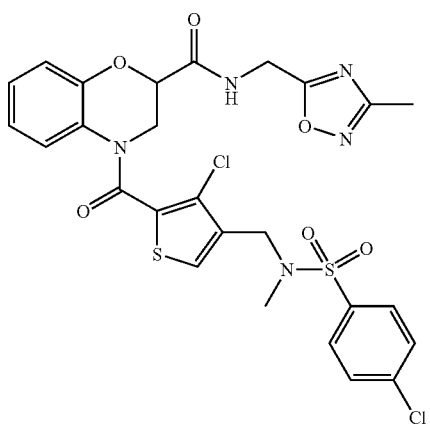

a) 4-Chlorobenzenesulfonyl chloride (10 g, 47 mmol) was added to a solution of methylamine hydrochloride (3.5 g, 52 mmol) and triethylamine (16.5 ml, 12.0 g, 119 mmol) in dichloromethane (100 ml) while cooling in an ice/water bath. The mixture was allowed to warm to room temperature and stirred for 18 h. The mixture was reduced and chromatography (30% EtOAc/70% hexanes) afforded 4-chloro-N-methylbenzenesulfonamide (7.9 g, 81%) as a colourless oil.

b) Sodium hydride (60% dispersion, 150 mg, 3.8 mmol) was added to a solution of 4-chloro-N-methylbenzenesulfonamide (640 mg, 3.1 mmol) in DMF (12 ml) while cooling in an ice/water bath. After stirring for 15 min the mixture was allowed to warm to room temperature and stirred for a further 30 min. Methyl 4-bromomethyl-3-chlorothiophene-2-carboxylate (1.08 g, 4.0 mmol) was added and the mixture was stirred for 18 h. 0.3N Potassium hydrogen sulphate solution was added and the mixture evaporated. The mixture was extracted with ethyl acetate and the organic extract was washed with brine, dried and reduced. Chromatography (25% EtOAc/75% 60-80 pet ether) yielded methyl 3-chloro(N-(4-chlorobenzenesulphonyl)-N-methylaminomethyl)thiophene-2-carboxylate (1.25 g, 79%) as a white solid.

c) Lithium hydroxide (210 mg, 5.0 mmol) and water (10 ml) were added to a solution of methyl 3-chloro-4-(N-(4-chlorobenzenesulphonyl)-N-methylaminomethyl) thiophene-2-carboxylate (990 mg, 2.5 mmol) in dioxan (20 ml) and the mixture stirred for 18 h. The mixture was evaporated and 0.3N potassium hydrogen sulphate was added. The mixture was extracted with ethyl acetate and the organic extracts were washed with water and brine, dried and reduced to afford 3-chloro-4-(N-(4-chlorobenzenesulphonyl)-N-methylaminomethyl)thiophene-2-carboxylic acid (800 mg, 84%) as a white solid.

d) A solution of 3-chloro-4-(N-(4-chlorobenzenesulphonyl)-N-methylaminomethyl)-thiophene-2-carboxylic acid (57 mg, 0.15 mmol) in thionyl chloride (2 ml) and dichloromethane (5 ml) was heated at reflux for 1 h. The mixture was cooled and reduced in vacuo. The residue was added to a solution of N-(3-methyl-1,2,4-oxadiazol-5-ylmethyl)benzomorpholine-2-carboxamide (40 mg, 0.15 mmol) and triethylamine (42 µl, 0.30 mmol) in dichloromethane (10 ml) and stirred at room temperature for 3 days. The mixture was reduced and chromatography (30% EtOAc/70% hexanes and 100% EtOAc) afforded 4-(3-chloro-4-(N-(4-chlorobenzenesulphonyl)-N-methylaminomethyl)thiophene-2-carbonyl)-N-(3-methyl-1,2,4-oxadiazol-5-ylmethyl)benzomorpholine-2-carboxamide as a colourless oil (31 mg, 33%).

$^1$H NMR (CDCl$_3$), 2.37 (3H, s), 2.65 (3H, s), 4.01 (1H, dd, J=6.9 Hz, 13.3 Hz), 4.09 (2H, s), 4.38 (1H, dd, J=3.0 Hz, 13.3 Hz), 4.72 (1H, dd, J=5.4 Hz, 17.3 Hz), 4.82 (1H, dd, J=6.2 Hz, 17.3 Hz), 4.91 (1H, dd, J=3.0 Hz, 6.9 Hz), 6.81-6.92 (1H, m), 7.03-7.14 (3H, m), 7.28 (1H, s), 7.51 (1H, s) 7.52 (2H, d, J=8.4 Hz), 7.74 (2H, d, J=8.4 Hz).

APCl MS m/z=635.9 (MH$^+$).

Example 3

4-(3-Chloro-4-(N-(4-chlorobenzenesulphonyl)-N-methylaminomethyl)thiophene-2-carbonyl)-N-(2-hydroxyethyl)benzomorpholine-2-carboxamide

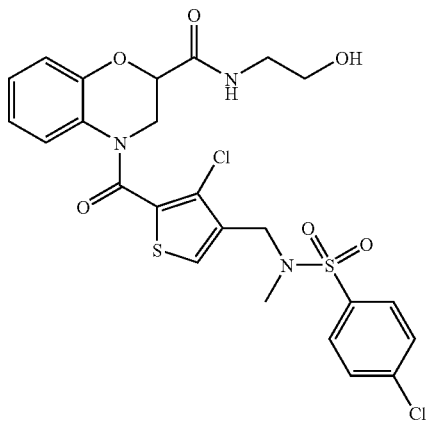

a) tert-Butyldimethylsilyl chloride (135 mg, 0.9 mmol) was added to a solution of N-(2-hydroxyethyl)benzomorpholine-2-carboxamide (185 mg, 0.83 mmol) and imidazole (61 mg, 0.90 mmol) in DMF (3 ml) while cooling in an ice/water bath. The mixture was allowed to warm to room temperature and stirred for 18 h. The mixture was reduced, taken up in ethyl acetate, washed with 0.3N potassium hydrogen sulphate and brine, filtered through phase separation paper and reduced. Chromatography (70% EtOAc/30% 60-80 petroleum ether) afforded N-(2-(tert-butyldimethylsilyloxyethyl)benzomorpholine-2-carboxamide (230 mg, 82%) as a brown gum.

b) 3-Chloro-4-(N-(4-chlorobenzenesulphonyl)-N-methylaminomethyl)thiophene-2-carboxylic acid (69 mg, 0.18 mmol) was dissolved in thionyl chloride (5 ml) and heated to reflux for 90 min. The mixture was cooled, reduced and dissolved in dichloromethane (5 ml). This solution was added to a solution of N-(2-(tert-butyldimethylsilyloxyethyl)benzomorpholine-2-carboxamide (61 mg, 0.18 mmol) and triethylamine (84 μl, 0.6 mmol) in dichloromethane (5 ml). The mixture was stirred for 1 h and reduced. Chromatography (40% EtOAc/60% 60-80 petroleum ether) afforded N-(2-tert-butyldimethylsilyloxyethyl)-4-(3-chloro-4-(N-(4-chlorobenzenesulphonyl)-N-methylaminomethyl)thiophene-2-carbonyl)benzomorpholine-2-carboxamide (65 mg, 52%) as a white solid.

c) A solution of tetrabutylammonium fluoride in THF (1.0M, 1.0 ml, 11.0 mmol) was added to a solution of N-(2-tert-butyldimethylsilyloxyethyl)-4-(3-chloro-4-(N-(4-chlorobenzenesulphonyl)-N-methylaminomethyl)thiophene-2-carbonyl)benzomorpholine-2-carboxamide (65 mg, 0.093 mmol) in THF (4.0 ml) and stirred for 1 h. The mixture was reduced, taken up in ethyl acetate, washed with 1N hydrochloric acid and brine, filtered and reduced. Chromatography (95% 60-80 petroleum ether/5% EtOAc) afforded 4-(3-chloro-4-(N-(4-chlorobenzenesulphonyl)-N-methylaminomethyl)thiophene-2-carbonyl)-N-(2-hydroxyethyl)-benzomorpholine-2-carboxamide as a white solid (25 mg, 46%).

$^1$H NMR (CDCl$_3$), 2.67 (3H, s), 3.36-3.46 (2H, m), 3.64-3.70 (2H, m), 4.09-4.16 (4H, m), 4.85 (1H, t, J=4.2 Hz), 6.85-6.90 (2H, m), 7.01-7.10 (2H, m), 7.25-7.29 (1H, m), 7.51 (1H, s), 7.53 (2H, d, J=8.4 Hz), 7.74 (2H, d, J=8.4 Hz).

APCl MS m/z=584 (MH$^+$).

Example 4

4-(3-Chloro-4-(N-(4-chloro-3-nitrobenzenesulphonyl)-N-methylaminomethyl)-thiophene-2-carbonyl)benzomorpholine

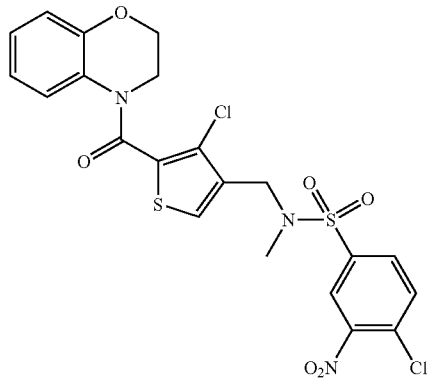

a) 1N Lithium hydroxide (aq) (7.0 ml, 7.0 mmol) was added to a solution of tert-butyl N-(3-chloro-2-(methyloxycarbonyl)thiophene-4-methyl)-N-methylcarbamate (1.52 g, 4.75 mmol) in dioxan (20 ml) and the mixture stirred at room temperature for 18 h. The mixture was diluted with ethyl acetate, acidified with 1N potassium hydrogen sulphate (aq) and separated. The organic phase was washed with water and brine, dried and reduced to afford tert-butyl N-(2-carboxy-3-chlorothiophene-4-methyl)-N-methylcarbamate as a colourless oil (1.38 g, 95%).

b) Benzomorpholine (405 mg, 3.0 mmol) and triethylamine (0.49 ml, 356 mg, 3.5 mmol) were added to a solution of tert-butyl N-(3-chloro-2-carboxythiophene-4-methyl)-N-methylcarbamate (0.73 g, 2.5 mmol) in dichloromethane (10 ml) and the mixture cooled in an ice/water bath. Pybrop® (1.4 g, 3.0 mmol) was added and the mixture stirred for 10 mins. The mixture was allowed to warm to room temperature and stirred for 3 days. The mixture was washed with water, dried over sodium sulfate and reduced. Chromatography (25% EtOAc/75% 6080 pet. ether) afforded a mixture of the product and unreacted benzomorpholine. The mixture was taken up in ethyl acetate, washed twice with 1N hydrochloric acid, once with brine, dried over sodium sulphate and reduced to yield tert-butyl N-(2-(benzomorpholine-4-carbonyl)-3-chlorothiophene-4-methyl)-N-methylcarbamate (0.70 g, 66%) as pale brown gum.

c) 4N Hydrogen chloride/dioxan solution (5 ml) was added to a solution of tert-butyl N-(2-(benzomorpholine-4-carbonyl)-3-chlorothiophene-4-methyl)-N-methylcarbamate (0.70 g, 1.7 mmol) in dioxan (10 ml) while cooling to 12° C. The mixture was allowed to warm to room temperature and stirred for 18 h. The mixture was reduced in vacuo and azeotroped with toluene and 60-80 pet. ether to yield 4-(3-chloro-4-(methylaminomethyl)thiophene-2-carbonyl)benzomorpholine hydrochloride (0.58 g, 95%) as white solid.

d) 4-Chloro-3-nitrobenzenesulfonyl chloride (0.46 g, 1.8 mmol) was added to a solution of 4-(3-chloro-4-(methylaminomethyl)thiophene-2-carbonyl)benzomorpholine hydrochloride (0.54 g, 1.49 mmol) and triethylamine (0.50 ml, 0.36 g, 3.6 mmol) in dichloromethane (20 ml) while cooling in an ice/water bath. The mixture was allowed to warm to room temperature and stirred for 3 days. The mixture was reduced and chromatographed to afford 4-(3-chloro(N-(4-chloro-3-nitrobenzenesulphonyl)-N-methylaminomethyl) thiophene-2-carbonyl)benzomorpholine (0.61 g, 76%) as a white crystalline solid.

$^1$H NMR (d$_6$ DMSO) 2.61 (3H, s), 3.86-3.98 (2H, m), 4.17 (2H, s), 4.30-4.40 (2H, m), 6.75 (1H, dt, J=1.5, 8.4 Hz), 6.91 (1H, dd, J=1.5, 8.4 Hz), 7.05 (1H, dt, J=1.5, 8.4 Hz), 7.20 (1H, d, J=8.4 Hz), 7.85 (1H, s), 8.04 (1H, d, J=8.4 Hz), 8.10 (1H, dt, J=2.0, 8.4 Hz), 8.50 (1H, d, J=2.0 Hz). ESIMS m/z 541.6 (MH$^+$).

Example 5

4-(4-(N-(3-Amino-4-chlorobenzenesulphonyl)-N-methylaminomethyl)-3-chlorothiophene-2-carbonyl) benzomorpholine

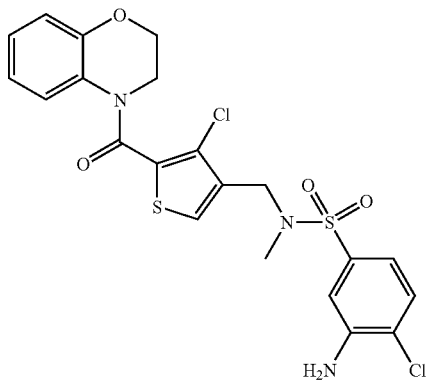

A mixture of 4-(3-chloro-4-(N-(4-chloro-3-nitrobenzene-sulphonyl)-N-methylaminomethyl)-thiophene-2-carbonyl) benzomorpholine (200 mg, 0.37 mmol) and zinc powder (400 mg) in glacial acetic acid (10 ml) was heated at 100° C. for 5 h. The mixture was cooled in an ice/water bath and diluted with water. Sodium hydroxide pellets (5 g) were added slowly to give pH=14. The mixture was extracted with dichloromethane, dried over sodium sulfate and reduced. Flash chromatography (35% EtOAc/65% 60-80 pet. ether) yielded a mixture of product and unreacted starting material. Preparative HPLC of this mixture afforded 4-(4-(N-(3-aminochlorobenzenesulphonyl)-N-methylaminomethyl)-3-chlorothiophene-2-carbonyl)benzomorpholine (102 mg, 54%) as a white solid.

$^1$H NMR (d$_6$ DMSO) 2.51 (3H, s), 3.92 (2H, t, J=4.3 Hz), 4.03 (2H, s), 4.34 (2H, J=4.3 Hz), 6.76 (1H, t, J=6.9 Hz), 6.88-6.96 (2H, m), 7.05 (1H, t, J=6.9 Hz), 7.18-7.30 (2H, m), 7.45 (1H, d, J=8.4 Hz), 7.86 (1H, s).

APCl MS m/z=512 (MH$^+$).

Example 6

1-(2-(N-(4-Bromobenzenesulphonyl)-N-methylaminomethyl)thiazole-4-carbonyl)-1,2,3,4-tetrahydroquinoline

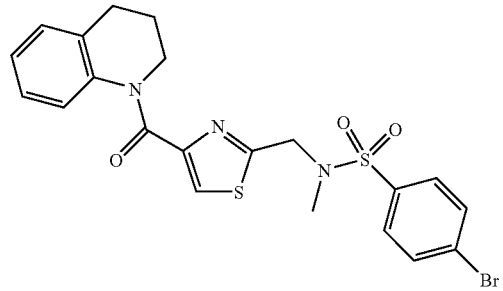

a) 4-Bromobenzenesulfonyl chloride (2.1 g, 8.2 mmol) was added to a solution of ethyl 2-(methylaminomethyl) thiazole-4-carboxylate (1.5 g, 7.5 mmol) and triethylamine (2.1 ml, 1.5 g, 15 mmol) in dichloromethane (30 ml) and the mixture was stirred for 18 h. The mixture was diluted with ethyl acetate and washed with 1N potassium hydrogen sulphate, water and brine, dried and reduced. Chromatography (35% EtOAc/65% hexanes) afforded ethyl 2-(N-(4-bromobenzenesulphonyl)-N-methylaminomethyl)thiazole-4-carboxylate (2.1 g, 67%) as a white solid.

b) Ethyl 2-(N-(4-bromobenzenesulphonyl)-N-methylaminomethyl)thiazole-4-carboxylate (2.19, 5.2 mmol) was added to mixture of 1N lithium hydroxide solution (10 ml, 10 mmol) and dioxan (20 ml) and heated to 50° C. until a solution was obtained. The mixture was stirred at room temperature for a further 3 days. The mixture was evaporated, taken up in EtOAc and acidified with 1N potassium hydrogen sulphate solution. The phases were separated and the organic phase washed with water and brine, dried and reduced to afford 2-(N-(4-bromobenzenesulphonyl)-N-methylaminomethyl)thiazole-4-carboxylic acid (1.86 g, 95%) as a white solid.

c) Thionyl chloride (2.0 ml) was added to a solution of 2-(N-(4-bromobenzenesulphonyl)-N-methylaminomethyl) thiazole carboxylic acid (460 mg, 1.2 mmol) in dichloromethane (20 ml) and the solution heated at reflux for 2 h. The mixture was cooled to room temperature, reduced in vacuo and azeotroped with toluene to yield a white solid. This was dissolved in dichloromethane (20 ml) and to it were added triethylamine (0.34 ml, 250 mg, 2.4 mmol) and 1,2,3,4-tetrahydroquinoline (0.18 ml, 190 mg, 1.4 mmol). After stirring for 1 h the mixture was reduced in vacuo. Chromatography (50% EtOAc/50% hexanes) afforded 1-(2-(N-(4-bromobenzenesulphonyl)-N-methylaminomethyl) thiazole-4-carbonyl)-1,2,3,4-tetrahydroquinoline (580 mg, 97%) as a white solid.

$^1$H NMR (CDCl$_3$), 1.98 (2H, quintet, J=6.6 Hz), 2.60 (3H, s), 2.75 (2H, t, J=6.6 Hz), 3.87 (2H, t, J=6.6 Hz), 4.36 (2H, s), 6.62-6.78 (1H, m), 6.85-6.90 (1H, m) 6.95 (1H, dt, J=1.3, 7.3 Hz), 7.08 (1H, d, J=7.3 Hz), 7.59-7.64 (4H, m), 7.65 (1H, s). ESIMS m/z=506.1, 508.1 (50:50 MH$^+$).

Example 7

4-Bromo-N-methyl-N-(3-(pyrido[3,2-b]morpholine-1-carbonyl)benzyl)benzenesulphonamide

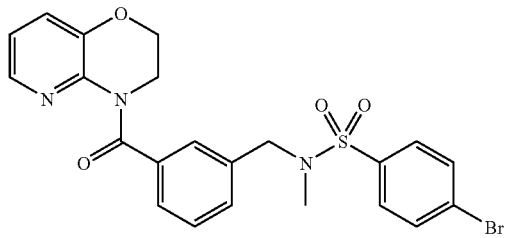

a) WSC.HCl (470 mg, 2.5 mmol) and 4-(dimethylamino) pyridine (290 mg, 2.4 mmol) were added to a solution of tert-butyl N-(3-carboxybenzyl)-N-methylcarbamate (520 mg, 2.0 mmol) and pyrido[3,2-b]morpholine (290 mg, 2.1 mmol) in dichloromethane (25 ml). The mixture was heated at reflux for 18 h. The mixture was concentrated in vacuo, taken up in ethyl acetate, washed with water and brine, dried and reduced. Chromatography (40% EtOAc/60% 60-80 pet.ether) afforded tert-butyl N-methyl-N-(3-(pyrido[3,2-b]morpholine-1-carbonyl)benzyl)carbamate (700 mg, 94%) as a colourless oil.

b) A solution of tert-butyl N-methyl-N-(3-(pyrido[3,2-b]morpholine-1-carbonyl)benzyl)-carbamate (610 mg, 1.6 mmol) in 4N hydrogen chloride/dioxan (30 ml) was stirred for 1 h. The mixture was reduced in vacuo to afford 1-(3-(methylaminomethyl)benzoyl)pyrido[3,2-b]morpholine dihydrochloride (512 mg, 100%) as a white solid.

c) 4-Bromobenzenesulphonyl chloride (31 mg, 0.12 mmol) was added to a solution of 1-(3-(methylaminomethyl)benzoyl)pyrido[3,2-b]morpholine dihydrochloride (35 mg, 0.11 mmol) in dichloromethane (20 ml). The pH was adjusted to pH9 with triethylamine and the mixture stirred for 18 h. The mixture was reduced in vacuo, taken up in ethyl acetate, washed with water and brine, dried and reduced. Chromatography (80% chloroform/20% cyclohexane) afforded 4-bromo-N-methyl-N-(3-(pyrido[3,2-b]morpholine-1-carbonyl)benzyl)benzene-sulphonamide (42 mg, 77%) as an off-white solid.

$^1$H NMR (CDCl$_3$), 2.49 (3H, s), 4.09 (2H, s), 4.13 (2H, t, J=4.6 Hz), 4.46 (2H, t, J=4.8 Hz), 6.87-6.91 (1H, m), 7.19-7.51 (5H, m), 7.52 (1H, d, J=1.6 Hz), 7.63-7.71 (4H, m). ESIMS m/z=502, 504 (50:50, MH$^+$)

Example 8

4-Bromo-N-methyl-N-(3-(1,2,3,4-tetrahydroqulnoxalin-3-one-1-carbonyl)benzyl)-benzene-sulphonamide

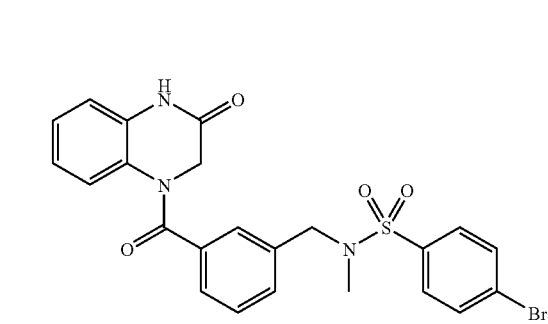

a) WSC.HCl (640 mg, 3.4 mmol) and 4-(dimethylamino) pyridine (330 mg, 2.7 mmol) were added to a solution of tert-butyl N-(3-carboxybenzyl)-N-methylcarbamate (700 mg, 2.6 mmol) and 1,2,3,4-tetrahydroquinoxalin-2-one (440 mg, 2.9 mmol) in dichloromethane (20 ml). The mixture was stirred for 18 h, reduced in vacuo and taken up in ethyl acetate. This solution was washed with 0.3N potassium hydrogen sulphate and saturated sodium hydrogen carbonate solutions, dried and reduced. Chromatography (50% EtOAc/50% 60-80 pet.ether) afforded tert-butyl N-(3-(1,2,3,4-tetrahydroquinoxalin-3-on-1-carbonyl) benzyl)-N-methylcarbamate (280 mg, 27%) as an orange oil.

b) A solution of tert-butyl N-(3-(1,2,3,4-tetrahydroquinoxalin-3-on-1-carbonyl)benzyl)-N-methylcarbamate (280 mg, 0.71 mmol) in 4N hydrogen chloride/dioxan (30 ml) was stirred at room temperature for 1 h. The mixture was reduced in vacuo, taken up in chloroform, washed with saturated sodium hydrogen carbonate solution and brine, dried and reduced. Chromatography (10% methanol/90% chloroform) afforded 1-(3-(methylaminomethyl)benzoyl-1,2,3,4-tetrahydroquinoxalin-3-one (98 mg, 49%) as an orange solid.

c) 4-Bromobenzenesulphonyl chloride (29 mg, 0.11 mmol) was added to a solution of 1-(3-(methylaminomethyl)benzoyl-1,2,3,4-tetrahydroquinoxalin-3-one (30 mg, 0.10 mmol) in dichloromethane (10 ml). The pH was adjusted to pH9 with triethylamine and the mixture stirred for 18 h. The mixture was reduced in vacuo, taken up in ethyl acetate, washed with water and brine, dried and reduced. Chromatography (50% EtOAc/50% 60-80 pet ether) afforded 4-bromo-N-methyl-N-(3-(1,2,3,4-tetrahydroquinoxalin-3-one-1-carbonyl)benzyl)-benzenesulphonamide (34 mg, 60%) as a white solid.

$^1$H NMR (CDCl$_3$), 2.46 (3H, s), 4.06 (2H, s), 4.59 (2H, s), 6.66 (1H, s), 6.76 (1H, t, J=7.6 Hz), 6.97 (1H, d, J=6.6 Hz), 7.06-7.12 (1H, m), 7.21 (1H, s), 7.31-7.43 (3H, m), 7.63-7.71 (4H, m), 8.97 (1H, s). ESIMS m/z=514, 516 (50:50, MH$^+$).

Example 9

3-Acetamido-1-(2-(N-bromobenzonesulphonyl)-N-methylaminomethyl)thiazole-4-carbonyl)-1,2,3,4-tetrahydroquinoline

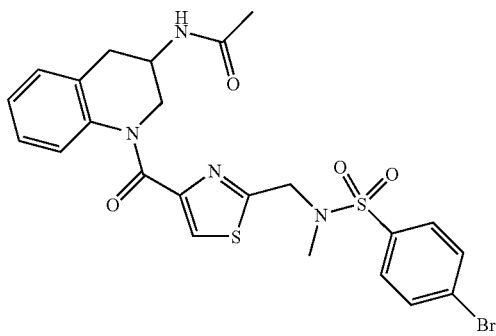

Thionyl chloride (5.0 ml) was added to a solution of 2-(N-(4-bromobenzenesulphonyl)-N-methylaminomethyl) thiazole-4-carboxylic acid (250 mg, 0.64 mmol) in dichloromethane (20 ml) and the solution was heated at reflux for 2 h. The mixture was cooled and reduced in vacuo to afford the acid chloride as a white solid. This acid chloride (130 mg, 0.32 mmol) was taken up in dichloromethane (10 ml) and to it were added 3-acetamido-1,2,3,4 tetrahydroquinoline (61 mg, 0.32 mmol) and triethylamine (0.089 ml, 65 mg, 0.64 mmol). The mixture was stirred at room temperature for 18 h and reduced in vacuo. Chromatography (EtOAc) afforded 3-acetamido-1-(2-(N-(4-bromobenzenesulphonyl)-N-methylaminomethyl)thiazole-4-carbonyl)-1,2,3,4-tetrahydroquinoline (96 mg, 53%) as a white solid.

$^1$H NMR (CDCl$_3$), 1.85 (3H, s), 2.61 (3H, s), 2.78 (1H, dd, J=3.6 Hz, 16.8 Hz), 3.21 (1H, dd, J=5.9 Hz, 16.8 Hz), 3.69 (1H, dd, J=3.0 Hz, 12.9 Hz), 4.30-4.35 (3H, m), 4.55-4.60 (1H, m), 6.02 (1H, d, J=7.6 Hz), 6.97-7.15 (3H, m), 7.15-7.20 (1H, m), 7.66 and 7.69 (each 2H, each d, J=3.6 Hz), 7.88 (1H, s). ESIMS m/z=563.0, 565.0 (50:50, MH$^+$).

Example 10

1-(2-(1-(4-Bromobenzenesulphonylamino)ethyl)thiazole-4-carbonyl)-1,2,3,4-tetrahydroquinoline

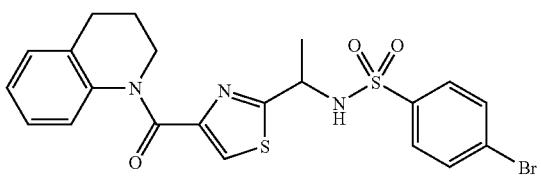

a) HBTU (306 mg, 0.81 mmol) was added to a solution of tert-butyl(1-(4-carboxythiazol-2-yl)ethyl)carbamate (200 mg, 0.73 mmol) in DMF (5 ml) at room temperature. Diisopropylethylamine (0.26 ml, 190 mg, 1.5 mmol) and 1,2,3,4-tetrahydroquinoline (0.11 ml, 117 mg, 0.88 mmol) were added and the mixture was stirred for 18 h. The mixture was partitioned between ethyl acetate and 1N hydrochloric acid and separated. The organic layer was washed with water and brine, dried and reduced. Chromatography (45% EtOAc/55% hexanes) afforded tert-butyl(1-(4-(1,2,3,4-tetrahydroquinoline-1-carbonyl) thiazol-2-yl)ethyl)carbamate (180 mg, 63%).

b) A solution of tert-butyl(1-(4-(1,2,3,4-tetrahydroquinoline-1-carbonyl)thiazol-2-yl)ethyl)-carbamate (180 mg, 0.47 mmol) in 4N hydrogen chloride/dioxan (10 ml) was stirred in an ice/water bath and allowed to warm to room temperature. The mixture was concentrated and azeotroped with toluene twice, tetrachloromethane twice and dichloromethane once to afford 1-(2-(1-aminoethyl)thiazole-4-carbonyl)-1,2,3,4-tetrahydroquinoline hydrochloride. The yield was assumed to be quantitative and the material was used directly by taking up in dichloromethane (5 ml) and triethylamine (0.16 ml, 118 mg, 1.2 mmol). The resulting solution was cooled in an ice/water bath and to it was added 4-bromobenzenesulphonyl chloride (119 mg, 0.47 mmol). The mixture was allowed to warm to room temperature and stirred for 18 h. Evaporation and chromatography (50% EtOAc/50% hexanes) afforded 1-(2-(1-(4-bromobenzenesulphonylamino)ethyl)thiazole-4-carbonyl)-1,2,3,4-tetrahydroquinoline as a white solid (144 mg, 61%).

$^1$H NMR (CDCl$_3$), 1.38 (3H, d, J=6.9 Hz), 2.05 (2H, dt, J=3.3 Hz, 6.6 Hz), 2.79-2.84 (2H, m), 3.80-4.01 (2H, m), 4.56 (1H, quintet, J=6.9 Hz), 5.29 (1H, d, J=7.6 Hz), 6.63-6.79 (1H, br m), 6.94 (1H, t, J=7.6 Hz), 7.07 (1H, dt, J=1.3 Hz, 7.6 Hz), 7.18 (1H, d, J=7.6 Hz), 7.58 (2H, d, J=8.9 Hz), 7.59 (1H, s), 7.64 (2H, d, J=8.9 Hz). ESIMS m/z=506.0, 507.9 (50:50, MH$^+$).

Examples 11-70

The following compounds were prepared using analogous methods.

| Ex. | R$^1$ | R$^2$ | R$^8$ | R$^{11}$ | R$^{12}$ | W | X | [M + H]$^+$ |
|---|---|---|---|---|---|---|---|---|
| 12 | H | H | Br | H | H | CH | CH$_2$ | 539.0 |
| 13 | H | H | Br | H | H | N | O | 541.9 |
| 14 | H | H | Cl | CH$_2$NMe$_2$ | H | CH | O | 553.9 |
| 15 | H | H | Cl | H | F | CH | O | 514.9 |
| 16 | Me | Me | Cl | H | H | CH | NH | 524.0 |
| 17 | =O | | Br | H | H | CH | NH | 554.1 |

-continued

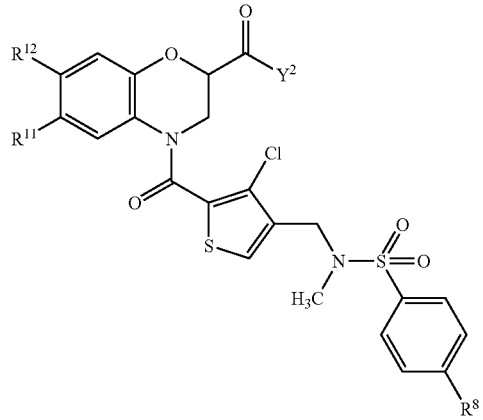

| Ex. | Y² | R⁸ | R¹¹ | R¹² | [M + H]⁺ |
|---|---|---|---|---|---|
| 18 | OH | Br | H | H | 584.9 |
| 19 | NHMe | Br | H | H | 598.0 |
| 20 | NHCH₂CH₂OH | Br | H | H | 627.9 |
| 21 | NHCH₂CH₂OH | Cl | OMe | H | 630.9 |
| 22 | NHCH₂CH₂OH | Cl | H | F | 601.9 |
| 23 | NHCH₂CO₂Me | Br | H | H | 655.9 |
| 24 | NHCH₂CONHMe | Cl | H | H | 611.0 |
| 25 | NHCH₂CONHMe | Cl | OMe | H | 641.0 |
| 26 | 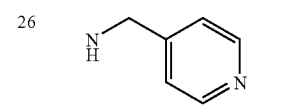 | Br | H | H | 674.9 |
| 27 | 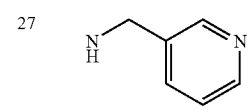 | Cl | H | H | 631.0 |
| 28 | 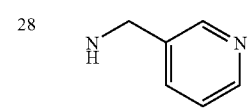 | Cl | OMe | H | 661.0 |
| 29 | 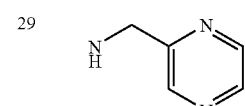 | Cl | OMe | H | 662.0 |
| 30 | 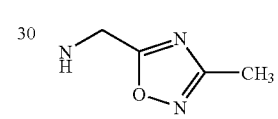 | Cl | OMe | H | 666.0 |
| 31 | 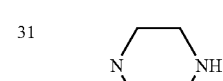 | Br | H | H | 653.0 |

-continued

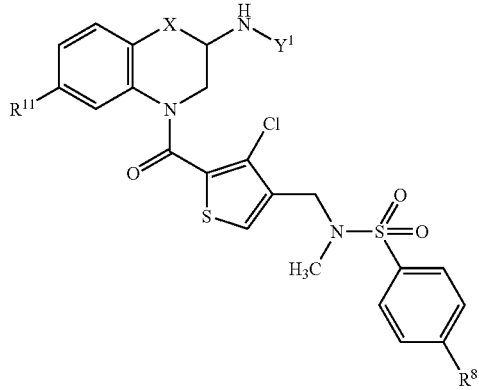

| Ex. | Y¹ | R⁸ | R¹¹ | X | [M + H]⁺ |
|---|---|---|---|---|---|
| 32 | C(=O)Me | Br | H | CH₂ | 596.1 |
| 33 | C(=O)CH₂NHMe | Br | H | CH₂ | 625.0 |
| 34 | C(=O)(CH₂)₂NH₂ | Br | H | CH₂ | 625.0 |
| 35 | C(=O)(CH₂)₂NH₂ | Br | H | O | 627.0 |
| 36 | C(=O)(CH₂)₂NH₂ | Cl | OMe | O | 613.0 |
| 37 | C(=O)(CH₂)₃NH₂ | Br | H | CH₂ | 639.0 |
| 38 | C(=O)(CH₂)₃NH₂ | Br | H | O | 641.0 |
| 39 | C(=O)(CH₂)₃NHMe | Br | H | CH₂ | 653.0 |
| 40 | C(=O)(CH₂)₂NHC(=O)Me | Br | H | CH₂ | 668.9 |
| 41 | C(=O)(CH₂)₃NHC(=O)Me | Br | H | CH₂ | 682.9 |
| 42 | C(=O)(CH₂)₃NHC(=O)NHEt | Br | H | CH₂ | 711.9 |

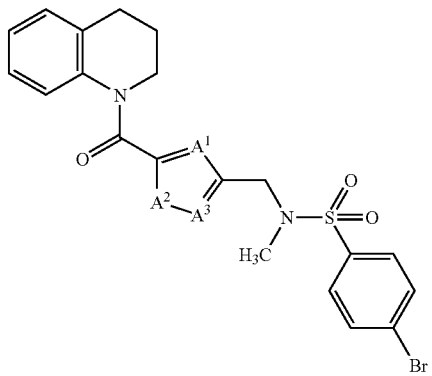

| Ex. | A¹ | A² | A³ | [M + H]⁺ |
|---|---|---|---|---|
| 43 | CH | S | CH | 504.9 |
| 44 | CH | N(CH₂CH₃) | N | 517.1 |
| 45 | C(NMe₂) | S | CH | 548.1 |

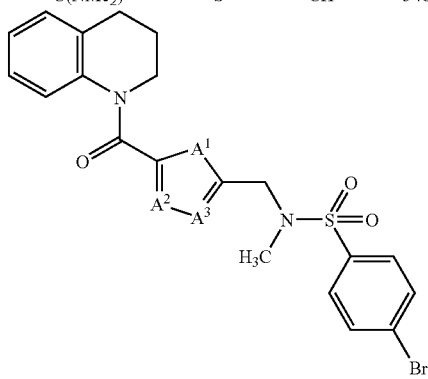

| Ex. | A¹ | A² | A³ | [M + H]⁺ |
|---|---|---|---|---|
| 46 | S | CH | CH | 505.1 |

-continued

| | | | | |
|---|---|---|---|---|
| 47 | O | CH | CH | 489 |
| 48 | S | CH | N | 505.9 |

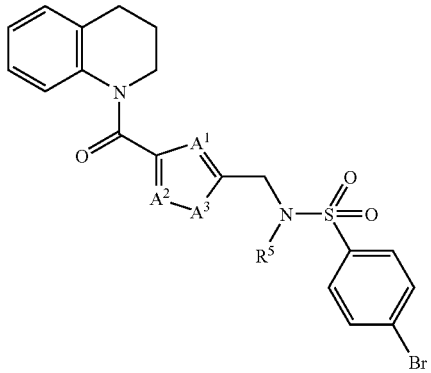

| Ex. | R⁵ | A¹ | A² | A³ | [M + H]⁺ |
|---|---|---|---|---|---|
| 49 | H | N | CH | S | 492.0 |
| 50 | Me | N | CH | O | 490.1 |
| 51 | Me | N | CH | NH | 489.0 |
| 52 | Me | N | CH | NMe | 502.9 |
| 53 | Me | N | C(Et) | S | 534.2 |
| 54 | Me | CH | N | O | 490.1 |
| 55 | Me | CH | N | NMe | 503.0 |

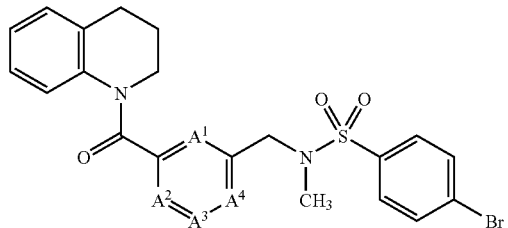

| Ex. | A¹ | A² | A³ | A⁴ | [M + H]⁺ |
|---|---|---|---|---|---|
| 56 | CH | CH | CH | C(OMe) | 529.1 |
| 57 | CH | CH | N | CH | 500 |
| 58 | CH | CH | CH | N | 500 |
| 59 | CH | CH | C(Me) | N | 514 |
| 60 | C(NO₂) | CH | CH | CH | 544.2 |
| 61 | C(NH₂) | CH | CH | CH | 514.3 |
| 62 | N | CH | CH | CH | 499.9 |
| 63 | CH | C(Cl) | CH | CH | 533.1 |
| 64 | C(Cl) | CH | CH | CH | 533 |
| 65 | CH | C(NH₂) | CH | CH | 514 |
| 66 | CH | C(OH) | CH | CH | 515.0 |
| 67 | CH | C(F) | CH | CH | 517 |
| 68 | CH | C(NO₂) | CH | CH | 544 |
| 69 | CH | C(Br) | CH | CH | 577 |
| 70 | CH | CH | CH | C(Cl) | 533.1 |

The compounds described above displace radiolabelled ligand from GnRH receptor-containing membrane preparations at concentrations below 5 μM.

The invention claimed is:

1. A compound of formula 1, or a pharmaceutically acceptable salt thereof,

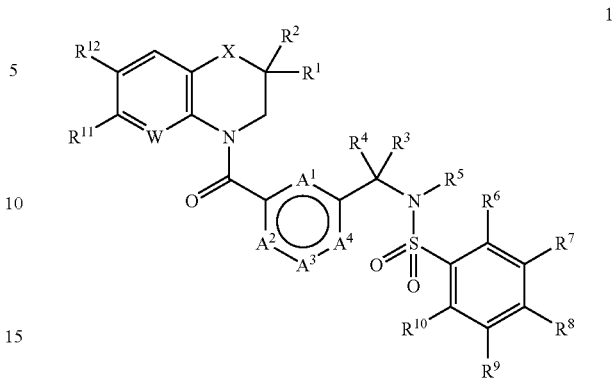

wherein:
A¹, A² and A³ are each independently selected from A⁵ and A⁶; and
A⁴ is either a covalent bond or A⁵; provided that
when A⁴ is a covalent bond then one of A¹-A³ is A⁶ and the other two are A⁵ and that
when A⁴ is A⁵ then all of A¹-A³ are A⁵;
A⁵ is selected from C—R¹³ and N;
A⁶ is selected from N—R¹⁴, S and O;
R¹ is selected from H, NHY¹ and COY² and R² is H; or R¹ and R² are both methyl or together are =O;
R³, R⁴ and R⁵ are each independently H, lower alkyl or lower alkenyl;
R⁶, R⁷, R⁸, R⁹, R¹⁰, R¹¹ and R¹² are each independently selected from H, lower alkyl, lower alkenyl, NH₂, F, Cl, Br, O-alkyl, O-lower alkenyl, CH₂NMe₂ and CF₃;
R¹³ is selected from H, F, Cl, Br, NO₂, NH₂, OH, Me, Et, OMe, NMe₂ and CF₃;
R¹⁴ is selected from H, methyl and ethyl;
W is CH;
X is O;
Y¹ is selected from CO-lower alkyl, CO-lower alkenyl, CO(CH₂)ᵦY³, CO(CH₂)ᵦCOY³ and CO(CH₂)ᵦNH-COY³;
Y² is selected from OR¹⁵, NR¹⁶R¹⁷ and NH(CH₂)ᵪCOY³;
Y³ is selected from alkyl, lower alkenyl, OR¹⁵ and NR¹⁶R¹⁷;
R¹⁵ is selected from H, lower alkyl, lower alkenyl and (CH₂)ₐR¹⁸
R¹⁶ and R¹⁷ are each independently selected from H, lower alkyl, lower alkenyl and (CH₂)ₐR¹⁸, or together are —(CH₂)₂-Z-(CH₂)₂—;
R¹⁸ is selected from OH and phenyl, pyridyl, pyrimidinyl, pyrazinyl, furyl, thienyl, pyrrolyl, imidazolyl, pyrazolyl, oxazolyl, isoxazolyl, thiazolyl, isothiazolyl, triazolyl, oxadiazolyl and thiadiazolyl, each of which may optionally have a lower alkyl, lower alkenyl group substituent;
Z is selected from O, CH₂, S, SO₂, NH, N-lower alkyl and N-lower alkenyl;
a is 0-4; and
b and c are 1-3.

2. A compound according to claim 1 wherein R³ and R⁴ are both H.

3. A compound according to claim 1 wherein R⁵ is lower alkyl or lower alkenyl.

4. A compound according to claim 3 wherein R⁵ is methyl.

5. A compound according to claim 1 wherein A¹, A², A³ and A⁴ are all A⁵.

6. A compound according to claim 5 wherein at least three of $A^1$, $A^2$, $A^3$ and $A^4$ are =$CR^{13}$—.

7. A compound according to claim 6 wherein $A^1$, $A^3$ and $A^4$ are =CH— and $A^2$ is =$CR^{13}$—.

8. A compound according to claim 7 wherein $A^2$ is =CF— or =CCl—.

9. A compound according to claim 6 wherein one of $A^1$, $A^2$, $A^3$ and $A^4$ is =N— and the others are =CH—.

10. A compound according to claim 9 wherein $A^1$ is =N— and $A^2$, $A^3$ and $A^4$ are =CH—.

11. A compound according to claim 1 wherein $A^4$ is a covalent bond.

12. A compound according to claim 11 wherein $A^1$ is $A^5$.

13. A compound according to claim 12 wherein one of $A^2$ and $A^3$ is =CH— and the other is —S—.

14. A compound according to claim 1 wherein at least three of $R^6$ to $R^{10}$ are H.

15. A compound according to claim 14 wherein four of $R^6$ to $R^{10}$ are H and the other is F, Cl, Br or $CF_3$.

16. A compound according to claim 15 wherein $R^6$, $R^7$, $R^9$ and $R^{10}$ are H and $R^8$ is F, Cl, Br or $CF_3$.

17. A compound according to claim 1 wherein $R^1$ is $COY^2$ and $R^2$ is H.

18. A compound according to claim 17 wherein $Y^2$ is $NR^{16}R^{17}$ or $NHCH_2COY^3$.

19. A compound according to claim 18 wherein $Y^2$ is $NHCH^2R^{18}$ or $NHCH_2CONHCH_3$, and $R^{18}$ is pyridyl or 3-methyl-1,2,4-oxadiazol-5-yl.

20. A compound according to claim 1 selected from:
4-(3-Chloro-4-{{(4-chloro-benzenesulfonyl)-methyl-amino]-methyl}-thiophene-2-carbonyl)-3,4-dihydro-2H-benzo[1,4]oxazine-2-carboxylic acid (3-methyl-[1,2,4]oxadiazol-5-ylmethyl)-amide;
4-(3-Chloro-4{[(4-chloro-benzenesulfonyl)-methyl-amino]-methyl}-thiophene-2-carbonyl)-3,4-dihydro-2H-benzo[1,4]oxazine-2-carboxylic acid (2-hydroxy-ethyl)-amide;
4-Chloro-N-[4-chloro-5-(2,3-dihydro-benzo[1,4]oxazine-4-carbonyl)-thiophen-3-ylmethyl]-N-methyl-3-nitro-benzenesulfonamide-ylmethyl]-N-methyl-3-nitro-benzenesulfonamide;
3-Amino-4-chloro-N-[4-chloro-5-(2,3-dihydro-benzo[1,4]oxazine-4-carbonyl)-thiophen-3-ylmethyl]-N-methyl-benzenesulfonamide;
4-Chloro-N-[4-chloro-5-(7-fluoro-2,3-dihydro-benzo[1,4]oxazine-4-carbonyl)-thiophen-3-ylmethyl]-N-methyl-benzenesulfonamide;
4-(4-{[(4-Bromo-benzenesulfonyl)-methyl-amino]-methyl}-3-chloro-thiophene-2-carbonyl)-3,4-dihydro-2H-benzo[1,4]oxazine-2-carboxylic acid methylamide;
4-(5-{[(4-Bromo-benzenesulfonyl)-methyl-amino]-methyl}-4-chloro-thiophene-3-carbonyl)-3,4-dihydro-2H-benzo[1,4]oxazine-2-carboxylic acid (2-hydroxy-ethyl)-amide;
4-(3-Chloro-4-{[(4-chloro-benzenesulfonyl)-methyl-amino]-methyl}-thiophene-2-carbonyl)-6-methoxy-3,4-dihydro-2H-benzo[1,4]oxazine-2-carboxylic acid (2-hydroxy-ethyl)-amide;
4-(3-Chloro-4-{[(4-chloro-benzenesulfonyl)-methyl-amino]-methyl}-thiophene-2-carbonyl)-7-fluoro-3,4-dihydro-2H-benzo[1,4]oxazine-2-carboxylic acid (2-hydroxy-ethyl)-amide;
{[4-5{[(4-Bromo-benzenesulfonyl)-methyl-amino]-methyl}-4-chloro-thiophene-3-carbonyl)-3,4-dihydro-2H-benzo[1,4]oxazine-2-carbonyl]-amino}-acetic acid methyl ester;
4-(3-Chloro-4-{[(4-chloro-benzenesulfonyl)-methyl-amino]-methyl}-thiophene-2-carbonyl)-3,4-dihydro-2H-benzo[1,3]oxazine-2-carboxylic and methylcarbamoylmethyl-amide;
4-(3-Chloro-4-{[(4-chloro-benzenesulfonyl)-methyl-amino]-methyl}-thiophene-2-carbonyl)-6-methoxy-3,4-dihydro-2H-benzo[1,4]oxazine-2-carboxylic acid methylcarbamoylmethyl-amide;
4-(5-{[(4-Bromo-benzenesulfonyl)-methyl-amino]-methyl}-4-chloro-thiophene-3-carbonyl)-3,4-dihydro-2H-benzo[1,4]oxazine-2-carboxylic acid (pyridin-4-ylmethyl)-amide;
4-(3-Chloro-4-{[(4-chloro-benzenesulfonyl)-methyl-amino]-methyl}-thiophene-2-carbonyl)-3,4-dihydro-2H-benzo[1,4]oxazine-2-carboxylic acid (pyridin-3-ylmethyl)-amide;
4-(3-Chloro-4-{[(4-chloro-benzenesulfonyl)-methyl-amino]-methyl}-thiophene-2-carbonyl)-6-methoxy-3,4-dihydro-2H-benzo[1,4]oxazine-2-carboxylic acid (pyridin-3-ylmethyl)-amide;
4-(3-Chloro-4-{[(4-chloro-benzenesulfonyl)-methyl-amino]-methyl}-thiophene-2-carbonyl)-6-methoxy-3,4-dihydro-2H-benzo[1,4]oxazine-2-carboxylic acid (pyrazin-2-ylmethyl)-amide;
4-(3-Chloro-4-{[(4-chloro-benzenesulfonyl)-methyl-amino]-methyl}-thiophene-2-carbonyl)-6-methoxy-3,4-dihydro-2H-benzo[1,4]oxazine-2-carboxylic acid (3-methyl-[1,2,4]oxadiazol-5-ylmethyl)-amide;
4-(4-{[(4-Bromo-benzenesulfonyl)-methyl-amino]-methyl}-3-chloro-thiophene-2-carbonyl)-3,4-dihydro-2H-benzo[1,4]oxazine-2-carboxylic acid (2-amino-ethyl)-amide;
4-(3-Chloro-4-1[(4-chloro-benzenesulfonyl)-methyl-amino]-methyl}-thiophene-2-carbonyl)-6-methoxy-3,4-dihydro-2H-benzo[1,4]oxazine-2-carboxylic acid (2-amino-ethyl)-amide;
pharmaceutically accepted salts thereof.

21. A pharmaceutical composition comprising a compound according to claim 1, and a pharmaceutically acceptable carrier.

22. A composition according to claim 21, which is a tablet or capsule for oral administration.

23. A compound according to claim 1 having one or more stereogenic centres.

24. A process of preparation of a composition which is a compound of formula 1, or a pharmaceutically acceptable salt thereof,

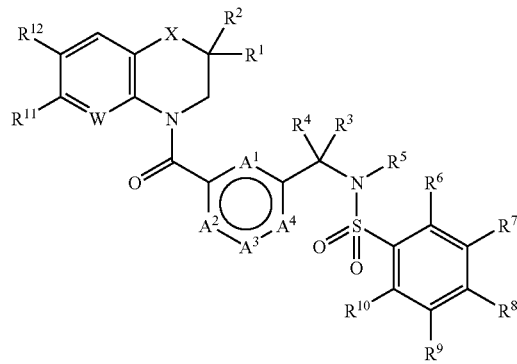

wherein:
  $A^1$, $A^2$ and $A^3$ are each independently selected from $A^5$ and $A^6$; and
  $A^4$ is either a covalent bond or $A^5$; provided that
    when $A^4$ is a covalent bond then one of $A^1$-$A^3$ is $A^6$ and the other two are $A^5$ and that
    when $A^4$ is $A^5$ then all of $A^1$-$A^3$ are $A^5$;
  $A^5$ is selected from C—$R^{13}$ and N;
  $A^6$ is selected from N—$R^{14}$, S and O;
  $R^1$ is selected from H, $NHY^1$ and $COY^2$ and $R^2$ is H; or $R^1$ and $R^2$ are both methyl or together are =O;
  $R^3$, $R^4$ and $R^5$ are each independently H, lower alkyl or lower alkenyl;
  $R^6$, $R^7$, $R^8$, $R^9$, $R^{10}$, $R^{11}$ and $R^{12}$ are each independently selected from H, lower alkyl, lower alkenyl, $NH_2$, F, Cl, Br, O-alkyl, O-lower alkenyl, $CH_2NMe_2$ and $CF_3$;
  $R^{13}$ is selected from H, F, Cl, Br, $NO_2$, $NH_2$, OH, Me, Et, OMe, $NMe_2$ and $CF_3$;
  $R^{14}$ is selected from H, methyl and ethyl;
  W is CH;
  X is O;
  $Y^1$ is selected from CO-lower alkyl, CO-lower alkenyl, $CO(CH_2)_bY^3$, $CO(CH_2)_bCOY^3$ and $CO(CH_2)_bNH\text{-}COY^3$;
  $Y^2$ is selected from $OR^{15}$, $NR^{16}R^{17}$ and $NH(CH_2)_cCOY^3$;
  $Y^3$ is selected from alkyl, lower alkenyl, $OR^{15}$ and $NR^{16}R^{17}$;
  $R^{15}$ is selected from H, lower alkyl, lower alkenyl and $(CH_2)_aR^{18}$
  $R^{16}$ and $R^{17}$ are each independently selected from H, lower alkyl, lower alkenyl and $(CH_2)_aR^{18}$, or together are —$(CH_2)_2$-Z-$(CH_2)_2$—;
  $R^{18}$ is selected from OH and phenyl, pyridyl, pyrimidinyl, pyrazinyl, furyl, thienyl, pyrrolyl, imidazolyl, pyrazolyl, oxazolyl, isoxazolyl, thiazolyl, isothiazolyl, triazolyl, oxadiazolyl and thiadiazolyl, each of which may optionally have a lower alkyl, lower alkenyl group substituent;
  Z is selected from O, $CH_2$, S, $SO_2$, NH, N-lower alkyl and N-lower alkenyl;
  a is 0-4; and
  b and c are 1-3;
which comprises the steps of:
  a) formation of an amide from a carboxylic acid and a cyclic amine; and
  b) formation of a sulphonamide from a sulphonyl chloride and an amine.

25. A process according to claim 24, in which step (a) comprises reaction of a compound of formula 7

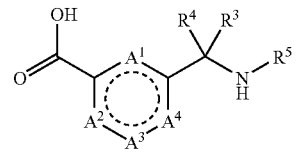

and a compound of formula 6

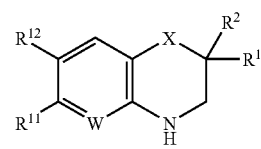

to obtain a compound of formula 9

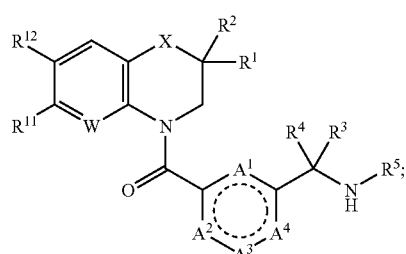

and step (b) comprises reaction of the compound of formula 9 with a compound of formula 8

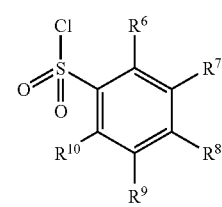

to form the compound of formula 1.

* * * * *